US006407077B1

(12) United States Patent
Gosselin et al.

(10) Patent No.: US 6,407,077 B1
(45) Date of Patent: Jun. 18, 2002

(54) β-L NUCLEOSIDES FOR THE TREATMENT OF HIV INFECTION

(75) Inventors: Gilles Gosselin; Jean-Louis Imbach, both of Montpellier (FR); Jean-Pierre Sommadossi, Birmingham, AL (US); Raymond F. Schinazi, Decatur, GA (US)

(73) Assignees: Emory University, Atlanta, GA (US); Centre National de la Recherche Scientifique, Paris (FR); The UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/435,268

(22) Filed: Nov. 5, 1999

Related U.S. Application Data

(60) Provisional application No. 60/107,178, filed on Nov. 5, 1998, and provisional application No. 60/115,862, filed on Jan. 13, 1999.

(51) Int. Cl.[7] ..................... A61K 31/7068; A61P 31/18
(52) U.S. Cl. ..................... 514/49; 536/26.7; 536/27.14
(58) Field of Search ..................... 514/49; 536/26.7, 536/27.14

(56) References Cited

U.S. PATENT DOCUMENTS 4,681,933 A    7/1987   Chu et al.

(List continued on next page.)

FOREIGN PATENT DOCUMENTS

DE       4224737       2/1994

(List continued on next page.)

OTHER PUBLICATIONS

Furman, et al., "The Anti–Hepatitis B Virus Activities, Cytoxicites, and Anabolic Profiles on the (–) and (+) Enantiomers of cis–5–Fluoro–1–[2–Hydroxymethyl)–1,3–oxathiolane–5–yl] Cytosine" *Antimicrobial Agents and Chemotherapy*, Dec. 1992, p. 2686–2692.

(List continued on next page.)

*Primary Examiner*—Edward J. Webman
*Assistant Examiner*—Helen Nguyen
(74) *Attorney, Agent, or Firm*—Sherry M. Knowles, Esq.; Josephine Young; King & Spalding

(57) ABSTRACT

Compounds and pharmaceutical compositions active against HIV are provided, as is a method for the treatment of HIV infection in humans and other host animals is provided comprising administering an effective amount of a β-L-(2' or 3'-azido)-2',3'-dideoxy-5-fluorocytosine of the formula

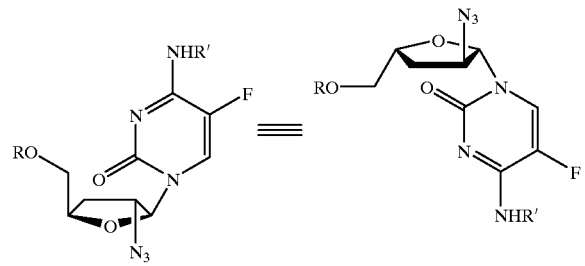

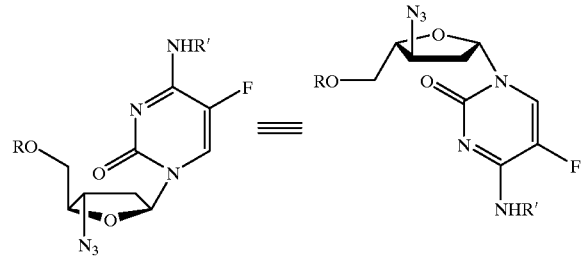

wherein R is H, acyl, monophosphate, diphosphate, or triphosphate, or a stabilized phosphate derivative (to form a stabilized nucleotide prodrug), and R' is H, acyl, or alkyl.

14 Claims, 6 Drawing Sheets

U.S. PATENT DOCUMENTS

| | | |
|---|---|---|
| 4,841,039 A | 6/1989 | Chu et al. |
| 4,916,122 A | 4/1990 | Chu et al. |
| 5,075,445 A | 12/1991 | Jarvest et al. ............... 544/276 |
| 5,077,279 A | 12/1991 | Chu et al. |
| 5,084,445 A | 1/1992 | Chu et al. |
| 5,142,051 A | 8/1992 | Holy et al. ................. 544/243 |
| 5,190,926 A | 3/1993 | Chu et al. |
| 5,444,063 A | 8/1995 | Schinazi ..................... 514/262 |
| 5,539,116 A | 7/1996 | Liotta et al. ................ 544/317 |
| 5,565,438 A | 10/1996 | Chu et al. ..................... 514/50 |
| 5,567,688 A | 10/1996 | Chu et al. ..................... 514/46 |
| 5,587,362 A | 12/1996 | Chu et al. ..................... 514/46 |
| 5,641,763 A | 6/1997 | Holy et al. .................... 514/80 |
| 5,684,010 A | 11/1997 | Schinazi ..................... 514/266 |
| 5,684,153 A | 11/1997 | Green et al. ................ 544/276 |
| 5,703,058 A | 12/1997 | Schinazi et al. ............. 514/45 |
| 5,814,639 A | 9/1998 | Liotta et al. ................ 514/274 |
| 5,914,331 A | 6/1999 | Liotta et al. ................ 514/274 |

FOREIGN PATENT DOCUMENTS

| | | |
|---|---|---|
| EP | 0 409 227 A2 | 1/1991 |
| EP | 0494119 | 7/1992 |
| WO | 92/18517 | 10/1992 |
| WO | WO 95/07086 | 3/1995 |
| WO | 95/07287 | 3/1995 |
| WO | 95/32984 | 12/1995 |
| WO | 96/13512 | 5/1996 |
| WO | 96/40164 | 12/1996 |
| WO | WO 97/09052 | 3/1997 |
| WO | WO 98/16186 | 4/1998 |

OTHER PUBLICATIONS

Cheng, et al., *Journal of Biological Chemistry*, vol. 267(20), 13938–13942 (1992).

Tsai, et al. in Biochem. Pharmacol. 48(7), pp. 1477–1481, 1994.

Mahmoudian, Pharm. Research 8(1), 43–6 (1991).

Gosselin G Et Al., "Anti–HIV Activities of the β–L Enantiomer of 2',3'–Dideoxycytidine and its 5–Fluoro Derivative in Vitro", Antimicrobial Agents and Chemotherapy, 38,6, Jun. 1994 pp. 1292–1297.

Lin et al., J. Med. Chem. 1998, 31, 336–340.

β-L NUCLEOSIDES FOR THE TREATMENT OF HIV INFECTION

This application claims priority to U.S. Ser. No. 60/107,178, filed on Nov. 5, 1998, and U.S. Ser. No. 60/115,862, filed on Jan. 13, 1999.

BACKGROUND OF THE INVENTION

This invention is in the area of methods for the treatment of human immunodeficiency virus (also referred to as "HIV") that includes administering to a host in need thereof, either alone or in combination, an effective HIV-treatment amount of one or more of the active compounds disclosed herein, or a pharmaceutically acceptable prodrug or salt of one of these compounds.

In 1981, acquired immune deficiency syndrome (AIDS) was identified as a disease that severely compromises the human immune system, and that almost without exception leads to death. In 1983, the etiological cause of AIDS was determined to be the human immunodeficiency virus (HIV).

In 1985, it was reported that the synthetic nucleoside 3'-azido-3'-deoxythymidine (AZT) inhibits the replication of human immunodeficiency virus. Since then, a number of other synthetic nucleosides, including (–)-β-2',3'-dideoxy-3'-thiacytidine (3TC), β-2',3'-dideoxy-3'-thia-5-fluorocytidine (FTC), 2',3'-dideoxyinosine (DDI), 2',3'-dideoxycytidine (DDC), and 2',3'-dideoxy-2',3'-didehydrothymidine (D4T), have been proven to be effective against HIV. After cellular phosphorylation to the 5'-triphosphate by cellular kinases, these synthetic nucleosides are incorporated into a growing strand of viral DNA, causing chain termination due to the absence of the 3'-hydroxyl group. They can also inhibit the viral enzyme reverse transcriptase.

The success of various synthetic nucleosides in inhibiting the replication of HIV in vivo or in vitro has led a number of researchers to design and test nucleosides that substitute a heteroatom for the carbon atom at the 3'-position of the nucleoside. European Patent Application Publication No. 0 337 713 and U.S. Pat. No. 5,041,449, assigned to BioChem Pharma, Inc., disclose racemic 2-substituted-4-substituted-1,3-dioxolanes that exhibit antiviral activity. U.S. Pat. No. 5,047,407 and European Patent Application Publication No. 0 382 526, also assigned to BioChem Pharma, Inc., disclose that a number of racemic 2-substituted-5-substituted-1,3-oxathiolane nucleosides have antiviral activity, and specifically report that the racemic mixture of 2-hydroxymethyl-5-(cytosin- 1-yl)- 1,3-oxathiolane (referred to as BCH-189) has approximately the same activity against HIV as AZT, with little toxicity. The (–)-enantiomer of the racemate BCH-189, known as 3TC, which is covered by U.S. Pat. No. 5,539,116 to Liotta et al., is currently sold for the treatment of HIV in humans in the U.S. in combination with AZT.

It has also been disclosed that cis-2-hydroxymethyl-5-(5-fluorocytosin-1-yl)-1,3-oxathiolane ("FTC") has potent HIV activity. Schinazi, et al., "Selective Inhibition of Human Immunodeficiency viruses by Racemates and Enantiomers of cis-5-Fluoro-1-[2-(Hydroxymethyl)-1,3-Oxathiolane-5-yl] Cytosine" *Antimicrobial Agents and Chemotherapy*, November 1992, pp. 2423–2431. See also U.S. Pat. Nos. 5,210,085; 5,814,639; 5,728,575; 5,827,727; 5,914,331; WO 91/11186 and WO 92/14743.

WO 96/40164 filed by Emory University, UAB Research Foundation, and the Centre National de la Recherche Scientifique discloses a number of β-L-2',3'-dideoxynucleosides for the treatment of hepatitis B.

WO 95/07287 also filed by Emory University, UAB Research Foundation, and the Centre National de la Recherche Scientifique discloses 2' or 3' deoxy and 2',3'-dideoxy-β-L-pentofuranosyl nucleosides for the treatment of HIV infection.

WO96/13512 filed by Genencor International, Inc., and Lipitek, Inc., discloses the preparation of L-ribofuranosyl nucleosides as antitumor agents and virucides.

WO 095/32984 discloses lipid esters of nucleoside monophosphates as immunosuppresive drugs, DE4224737 discloses cytosine nucleosides and their pharmaceutical uses.

Tsai, et al., in Biochem. Pharmacol. 48(7), pages 1477–81, 1994 discloses the effect of the anti-HIV agent 2'-β-D-F-2',3'-dideoxynucleoside analogs on the cellular content of mitochondrial DNA and lactate production.

Galvez, J. Chem. Inf. Comput. Sci. (199 4), 35(5), 1198–203 describes molecular computation of β-D-3'-azido,-2',3'-dideoxy-5-fluorocytidine.

Mahmoudian, Pharm. Research 8(1), 43–6 (1991) discloses quantitative structure-activity relationship analyses of HIV agents such as β-D-3'-azido-2',3'-dideoxy-5-fluorocytidine.

U.S. Pat. No. 5,703,058 discloses (5-carboximido or 5-fluoro)-(2',3'-unsaturated or 3'-modified) pyrimidine nucleosides for the treatment of HIV and HBV infection.

Lin, et al., discloses the synthesis and antiviral activity of various 3'-azido analogues of β-D-nucleosides in J. Med. Chem. 31(2), 336–340 (1988).

In light of the fact that acquired immune deficiency syndrome and AIDS-related complex have reached epidemic levels worldwide, and have tragic effects on the infected patient, there remains a strong need to provide new effective pharmaceutical agents to treat these diseases that have low toxicity to the host.

It is an object of the present invention to provide a compound and method for the treatment of human patients or other host animals infected with HIV.

SUMMARY OF THE INVENTION

A method for the treatment of HIV infection in humans and other host animals is disclosed that includes administering an effective HIV-treatment amount to the host of a β-L-(2'or 3'-azido)-2',3'-dideoxy-5-fluorocytosine nucleoside or a pharmaceutically acceptable salt, ester, or prodrug thereof, including a stabilized phosphate, administered either alone or in combination or alternation with another anti-HIV agent, optionally in a pharmaceutically acceptable carrier. In a preferred embodiment, the 2'or 3'-azido group is in the ribosyl configuration.

The disclosed β-L-(2' or 3'-azido)-2',3'-dideoxy-5-fluorocytosine nucleosides, or pharmaceutically acceptable salts, esters, or prodrugs or pharmaceutically acceptable formulations containing these compounds are useful in the prevention and treatment of HIV infections and other related conditions such as Acquired Immune Deficiency Syndrome (AIDS), AIDS-Related Complex (ARC), persistent generalized lymphadenopathy (PGL), AIDS-related neurological conditions, anti-HIV antibody positive and HIV-positive conditions, Kaposi's sarcoma, thrombocytopenia purpurea and opportunistic infections. These compounds or formulations can also be used prophylactically to prevent or retard the progression of clinical illness in individuals who are anti-HIV antibody or HIV-antigen positive or who have been exposed to HIV.

In one embodiment, the active compound is β-L-(2'-azido)-2',3'-dideoxy-5-fluorocytosine (L-2'-A-5-FddC) or a pharmaceutically acceptable ester, salt or prodrug thereof of the formula:

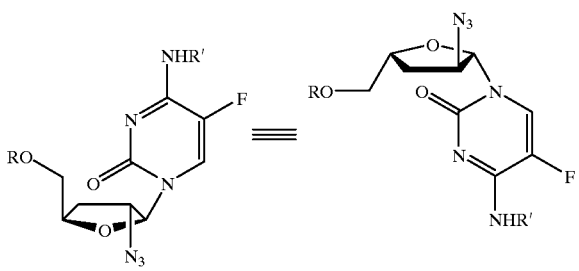

wherein R is H, acyl, monophosphate, diphosphate, or triphosphate, or a stabilized phosphate derivative (to form a stabilized nucleotide prodrug), and R' is H, acyl, or alkyl.

In another embodiment, the active compound is β-L-(3'-azido)-2',3'-dideoxy-5-fluorocytosine (L-3'-A-5-FddC) or a pharmaceutically acceptable ester, salt or prodrug thereof of the formula:

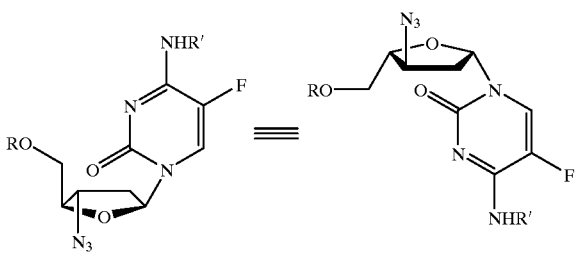

wherein R is H, acyl, monophosphaie, diphosphate, or triphosphate, or a gtabilized phosphate derivative (to form a stabilized nucleotide prodrug), and R' is H, acyl, or alkyl.

In another embodiment, the L-(2' or 3')-A-5-FddC nucleoside is administered in alternation or combination with one or more other compounds which exhibit activity against HIV, as described in more detail below. In general, during alternation therapy, an effective dosage of each agent is administered serially, whereas in combination therapy, an effective dosage of two or more agents are administered together. The dosages will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions. In one preferred embodiment, the compound is administered in combination with AZDU (3'-azido-2',3'-dideoxyuridine).

DETAILED DESCRIPTION OF THE INVENTION

Figure 1:
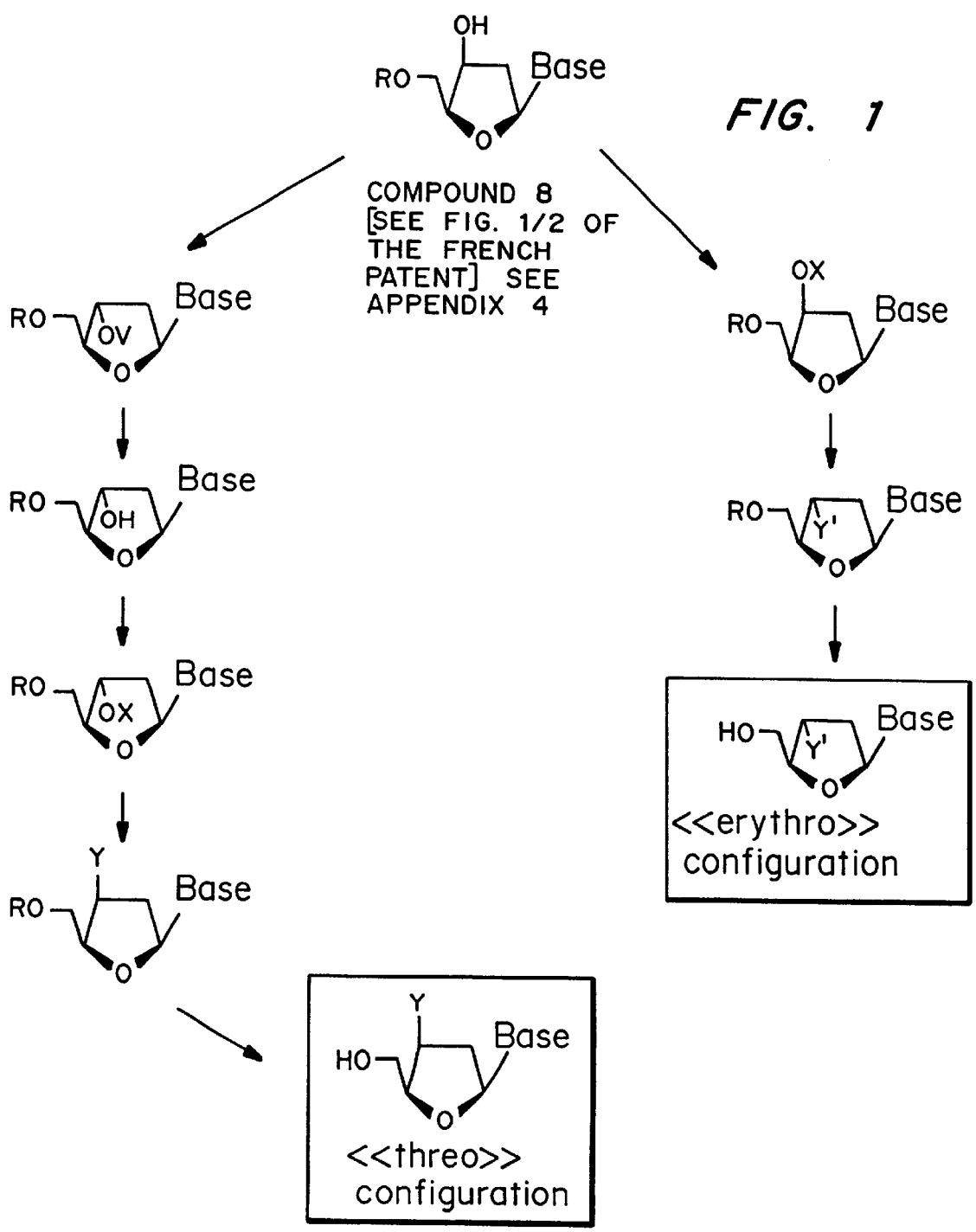
FIG. 1 is an illustration of a general reaction scheme for the stereospecific synthesis of 3'-substituted β-L-dideoxynucleosides.

A method for the treatment of HIV infection in humans and other host animals is disclosed that includes administering an effective amount of a β-L-(2'or 3'-azido)-2',3'-dideoxy-5-fluorocytosine nucleoside (referred to below as "L-(2' or 3')-A-5-FddC") or a pharmaceutically acceptable salt, ester, or prodrug thereof, including a stabilized phosphate, either alone or in combination or alternation with another anti-HIV agent, optionally in a pharmaceutically acceptable carrier.

The compounds described herein can be used to treat AIDS and AIDS-related conditions including Acquired Immune Deficiency Syndrome (AIDS), AIDS-Related Complex (ARC), persistent generaiezed lymphadenopatliy (PGL), AIDS-related neurological conditions, anti-HIV antibody positive and HIV-positive conditions, Kaposi's sarcoma, thrombocytopenia purpurea and opportunistic infections. The method of the present invention includes the use of an L-(2' or 3')-A-5-FddC prophylactically to prevent or retard the progression of clinical illness in individuals who are anti-HIV antibody or HIV-antigen positive or who have been exposed to HIV.

As used herein, the term "substantially in the form of a single isomer" "substantially free of" or "substantially in the absence of" refers to a nucleoside that is at least approximately 95% in the designated stereoconfiguration.

The term alkyl, as used herein, unless otherwise specified, refers to a saturated straight, branched, or cyclic, primary, secondary, or tertiary hydrocarbon of $C_1$ to $C_{10}$, and specifically includes methyl, ethyl, propyl, isopropyl, butyl, isobutyl, t-butyl, pentyl, cylcobutyl, cyclopropyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The alkyl group can be optionally substituted with one or more moieties selected from the group, consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991. The term lower alkyl, as used herein, and unless otherwise specified, refers to a $C_1$ to $C_4$ ethyl, propyl, butyl, pentyl, hexyl, isopropyl, isobutyl, sec-butyl, or t-butyl groupAs used herein, the term acyl refers to moiety of the formula -C(O)R', wherein R' is alkyl; aryl, alkaryl, aralkyl, heteroaromatic, alkoxyalkyl including methoxymethyl; arylalkyl including benzyl; amyloxyalkyl such as phenoxymethyl; aryl including phenyl optionally substituted with halogen, $C_1$ to $C_4$ alkyl or $C_1$ to $C_4$ alkoxy, or the residue of an amino acid. The term acyl specifically includes but is not limited to acetyl, propionyl, butyryl, pentanoyl, 3-methylbutyryl, hydrogen succinate, 3-chlorobenzoate, benzoyl, acetyl, pivaloyl, mesylate, propionyl, valeryl, caproic, caprylic, capric, lauric, myristic, palmitic, stearic, and oleic.

The L-(2' or 3')-A-5-FddC nucleoside can be converted into a pharmaceutically acceptable ester by reaction with an appropriate esterifying agent, for example, an acid halide or anhydride. The nucleoside or its pharmaceutically acceptable prodrug can be converted into a pharmaceutically acceptable salt thereof in a conventional manner, for example, by treatment with an appropriate base or acid. The ester or salt can be converted into the parent nucleoside, for example, by hydrolysis.

As used herein, the term pharmaceutically acceptable salts or complexes refers to salts or complexes of the L-(2'or 3')-A-5-FddC that retain the desired biological activity of the parent compound and exhibit minimal, if any, undesired toxicological effects. Nonlimiting examples of such salts are (a) acid addition salts formed with inorganic acids (for example, hydrochloric acid, hydrobromic acid, sulfuiric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acids, naphthalenedisulfonic acids, and polygalacturonic acid, (b) base addition salts formed with cations such as sodium, potassium, zinc, calcium, bismuth, barium, magnesium, aluminum, copper, cobalt, nickel, cadmium, sodium, potassium, and the like, or with an organic cation formed from N,N-dibenzylethylenediamine, ammonium, or ethylenediamine; or (c) combinations of (a) and (b); e.g., a zinc tannate salt or the like.

The term prodrug, as used herein, refers to a compound that is converted into the nucleoside on administration in vivo, or that has activity in itself. Nonlimiting examples are pharmaceutically acceptable salts (alternatively referred to as "physiologically acceptable salts"), and the 5' and $N^4$ acylated or alkylated derivatives of the active compound, as well as The 5'-monophosphate, diphosphate, or triphosphate derivatives or stablized phophate prodrugs (alternatively referred to as "physiologically or pharmaceutically acceptable derivatives") or phosphate lipid prodrugs, as described herein.

Modifications of the active compounds, specifically at the $N^4$ and 5'—O positions, can affect the bioavailability and rate of metabolism of the active species, thus providing control over the delivery of the active species.

A preferred embodiment of the present invention is a method for the treatment of HIV infections in humans or other host animals, that includes administering an effective amount of one or more of an L-(2' or 3')-A-5-FddC nucleoside selected from the group consisting of, L-2'-A-5-FddC, and L-3'-A-5-FddC, or a physiologically acceptable prodrug thereof, including a phosphate, 5' and or $N^4$ alkylated or acylated derivative, or a physiologically acceptable salt thereof, optionally in a pharmaceutically acceptable carrier. The compounds of this invention either possess anti-HIV activity, or are metabolized to a compound or compounds that exhibit anti-HIV activity. In a preferred embodiment, the L-(2' or 3')-A-5-FddC nucleoside is administered substantially in the form of a single isomer, i.e., at least approximately 95% in the designated stereoconfiguration.

Combination or Alternation Therapy

It has been recognized that drug-resistant variants of HIV can emerge after prolonged treatment with an antiviral agent. Drug resistance most typically occurs by mutation of a gene that encodes for an enzyme used in the viral life cycle. Recently, it has been demonstrated that the efficacy of a drug against HIV infection can be prolonged, augmented, or restored by administering the compound in combination or alternation with a second, and perhaps third, antiviral compound that induces a different mutation from that caused by the principle drug. Alternatively, the pharmacokinetics, biodistribution, or other parameter of the drug can be altered by such combination or alternation therapy. In general, combination therapy is typically preferred over alternation therapy because it induces multiple simultaneous stresses on the virus.

The second antiviral agent for the treatment of HIV, in one embodiment, can be a reverse transcriptase inhibitor (a "RTI"), which can be either a synthetic nucleoside (a "NRTI") or a non-nucleoside compound (a "NNRTI"). In an alternative embodiment, in the case of HIV, the second (or third) antiviral agent can be a protease inhibitor. In other embodiments, the second (or third) compound can be a pyrophosphate analog, or a fusion binding inhibitor. A list compiling resistance data collected in vitro and in vivo for a number of antiviral compounds is found in Schinazi, et al, Mutations in retroviral genes associated with drug resistance, *International Antiviral News*, Volume 1(4), International Medical Press 1996.

Preferred examples of antiviral agents that can be used in combination or alternation with the compounds disclosed herein for HIV therapy include 2-hydroxymethyl-5-(5-fluorocytosin-1-yl)-1,3-oxaiolaone (FTC); the (−)-enantiomer of 2-hydroxymethyl-5-(cytosin-1-yl)-1,3-oxathiolane (3TC); carbovir, acyclovir, interferon, AZT, DDI, DDC, D4T, CS-92 (3'-azido-2',3'-dideoxy-5-methyl-cytidine), and β-D-dioxolane nucleosides such as β-D-dioxolanyl-guanine (DXG), β-D-dioxolanyl-2,6-diaminopurine (DAPD), and β-D-dioxolanyl-6-chloropurine (ACP), MKC-442 (6-benzyl-1-(ethoxymethyl)-5-isopropyl uracil.

Preferred protease inhibitors include crixovan (Merck), nelfinavir (Agouron), ritonavir (Abbot), saquinavir (Roche), and DMP-450 (DuPont Merck).

Nonlimiting examples of compounds that can be administered in combination or alternation with any of the β-L-(2' or 3'-azido)-2',3'-dideoxy-5-fluorocytosines of the present invention include (1S, 4R)-4-[2-amino-6-cyclopropyl-amino)-9H-purin-9-yl]-2-cyclopentene-1-methanol succinate ("1592", a carbovir analog; GlaxoWellcome); 3TC (−)-β-L-2',3'-dideoxy-3'-thiacytidine (GlaxoWellcome); a-APA R18893: a-nitro-anilino-phenylacetarnide; A-77003; C2 symmetry-based protease inhibitor (Abbott); A-75925: C2 symmetry-based protease inhibitor (Abbott); AAP-BHAP: bisheteroarylpiperazine analog (Upjohn); ABT-538: C2 symmetry-based protease inhibitor (Abbott); AzddU: 3'-azido-2',3'-dideoxyuridine; AZT: 3'-azido-3'-deoxythymidine (GlaxoWellcome); AZT-p-ddI: 3'-azido-3'-deoxythymidilyl-(5',5')-2',3'-dideoxyinosinic acid (Ivax); BHAP: bisheteroarylpiperazine; BILA 1906: N-{1S-[[[3-[2S-{(1,1-dimethylethyl)amino]carbonyl}-4R-]3-pyridinylmethyl)thio]-1-piperidinyl]-2R-hydroxy-1S-(phenylmethyl)-propyl]amino]carbonyl]-2-methylpropyl}-2-quinolinecarboxamide (Bio Mega/Boehringer-Ingelheim); BILA 2185: N-(1,1-dimethylethyl)- 1-[2S-[[2–2,6-dimethyphenoxy)-1-oxoethyl]amino]-2R-hydroxy - 4-phenylbutyl]4R-pyridinylthio)-2-piperidinecarboxamide (Bio Mega/Boehringer-Ingelheim); BM+51.0836: thiazolo-isoindolinone derivative; BMS 186,318: aminodiol derivative HIV-1 protease inhibitor (Bristol-Myers-Squibb); d4API: 9-[2,5-dihydro-5-(phosphonomethoxy)-2-furanel] adenine (Gilead); d4C: 2',3'-didehydro-2',3'-dideoxycytidine; d4T: 2',3'-didehydro-3 '-deoxythymidine (Bristol-Myers-Squibb); ddC; 2',3'-dideoxycytidine (Roche); ddI: 2',3'-dideoxyinosine (Bristol-Myers-Squibb); DMP-266: a 1,4-dihydro-2H-3, 1-benzoxazin-2-one; DMP-450: {[4R-(4-a, 5-a, 6-b, 7-b)]-hexahydro-5,6-bis(hydroxy)-1,3-bis(3-amino)phenyl]methyl)-4,7-bis(phenylmethyl)-2H-1,3-diazepin-2-one}-bismesylate (Avid); DXG:(−)-β-D- dioxolane-guanosine (Triangle); EBU-dM:5-ethyl-1-ethoxymethyl-6-(3,5-dimethylbenzyl)uracil; E-EBU: 5-ethyl-1-ethoxymethyl-6-benzyluracil; DS: dextran sulfate; E-EPSeU: 1-(ethoxymethyl)-(6-phenylselenyl)-5-ethyluracil; E-EPU: 1-(ethoxymethyl)-(6-phenyl-thio)-5-ethyluracil; FTC: β-2',3'-dideoxy-5-fluoro-3'-thiacytidine (Triangle); HBY097: S-4-isopropoxycarbonyl-6-methoxy-3-(methylthio-methyl)-3,4-dihydroquinoxalin -2(1H)-thione; HEPT:1-[(2-hydroxyethoxy)methyl]6-(phenylthio) thymine; HIV-1:human immunodeficiency virus type 1; JM2763: 1,1'-(1,3-propanediyl)-bis-1,4,8,11-tetraazacyclotetradecane (JohnsonMatthey); JM3100:1,1'-[1,4-phenylenebis-(methylene)]-bis-1,4,8,11-tetraazacyclotetradecane(Johnson Matthey); KNI-272: (2S,3S)-3-amino-2-hydroxy-4-phenylbutyric acid-containing tripeptide; L-697,593; 5-ethyl-6-methyl-3-(2-phthalimidoethyl)pyridin-2(1H)-one; L-735,524: hydroxy-aminopentane amide HIV-1 protease inhibitor (Merck); L-697,661: 3-{[(-4,7-dichloro-1,3-benzoxazol-2-yl)methyl]amino}-5-ethyl-6-methylpyridin -2(1 H)-one; L-FDDC: (−)-β-L-5-fluoro-2',3'-dideoxycytidne; L-FDOC:(−)-β-L-5-fluoro-dioxolane cytosine; MKC442: 6-benzyl-1-ethoxymethyl-5-isopropyluracil (I-EBU; Triangle/Mitsubishi); Nevirapine: 11-cyclopropyl-5,11-dihydro-4-methyl-6H-dipyridol[3,2-b:2',3'-e]diazepin-6-one (Boehringer-Ingelheim); NSC648400: 1-benzyloxymethyl-5-ethyl-6-(alpha-pyridylthio)uracil (E-BPTU); P9941: [2-pyridylacetyl-IlePheAla-y(CHOH)]2 (Dupont Merck); PFA: phosphonoformate (foscarnet; Astra); PMEA: 9-(2-phosphonylmethoxyethyl)adenine (Gilead); PMPA: (R)-9-(2-phosphonyl-methoxypropyl)adenine (Gilead); Ro 31–8959: hydroxyethylamine derivative HIV- 1 protease inhibitor (Roche); RPI-312: peptidyl protease inhibitor, 1-[(3s)-3-(n-alpha-benzyloxycarbonyl)-1-asparginyl)-amino-2-hydroxy-4-phenylbutyryl]-n-tert-butyl-1-proline amide; 2720: 6-chloro-3,3-dimethyl-4-(isopropenyloxycarbonyl)-3,4-dihydro-quinoxalin-2(1H) thione; SC-52151: hydroxyethylurea isostere protease inhibitor (Searle); SC-55389A: hydroxyethyl-urea isostere protease inhibitor (Searle); TIBO R82150: (+)-(5S)-4,5,6,7-tetrahydro-5-methyl-6-(3-methyl-2-butenyl)imidazo[4,5,1-jk][1,4]-benzodiazepin-2(1H) thione (Janssen); TIBO 82913: (+)-(5S)-4,5,6,7,-tetrahydro-9-chloro-5-methyl-6-(3-methyl-2-butenyl)imidazo[4,5,1jk]-[1,4]benzo-diazepin-2(1H)-thione (Janssen); TSAO-m3T:[2',5-bis-O-(tert-butyldimethylsilyl)-3 '-spiro-5 '-(4'-amino-1',2'-oxathiole-2', 2'-dioxide)]-b-D-pentofiranosyl-N3-methylthymine: U90152: 1-[3-[(1-methylethyl)-amino]-2-pyridinyl]-4-[[5-[(methylsulphonyl)-amino]-1H -indol-2yl]carbonyl] piperazine; UC: thiocarboxanilide derivatives (Uniroyal); UC-781=N-[4-chloro-3-(3-methyl-2-butenyloxy)phenyl]-2-methyl-3-furancarbothioamide; UC -82=N-[4-chloro-3-(3-methyl-2-butenyloxy)phenyl]-2-methyl-3-thiophenecarbothioamide; VB 11,328: hydroxyethyl-sulphonamide protease inhibitor (Vertex); VX-478: hydroxyethylsulphonamide protease inhibitor (Vertex); XM 323: cyclic urea protease inhibitor (Dupont Merck) or DMP - 266 (efavirenz, Sustiva).

Preparation of the Active Compounds

Stereochemistry

Since the 1'and 4'carbons of the sugar or dioxolanyl moiety (referred to below generically as the sugar moiety) of the nucleosides are chiral, their nonhydrogen substituents ($CH_2OR$ and the pyrimidine or purine base, respectively) can be either cis (on the same side) or trans (on opposite sides) with respect to the sugar ring system. The four optical isomers therefore are represented by the following configurations (when orienting the sugar moiety in a horizontal plane such that the "primary" oxygen (that between the C1 and C4'-atoms is in back): "β" or "cis" (with both groups "up", which corresponds to the configuration of naturally occurring nucleosides, i.e., the D configuration), "β" or cis (with both groups "down", which is a nonnaturally occurring configuration, i.e., the L configuration), "α" or "trans" (with the C2 substituent "up" and the C5 substituent "down"), and trans (with the C2 substituent "down" and the C5 substituent "up").

The active nucleosides of the present invention are in the β-L-configuration, with the azido group in the ribosyl configuration.

Nucleotide Prodrugs

Any of the nucleosides described herein can be administered as a stabilized nucleotide prodrug to increase the activity, bioavailability, stability or otherwise alter the properties of the nucleoside. A number of nucleotide prodrug ligands are known. In general, alkylation, acylation or other lipophilic modification of the mono, di or triphosphate of the nucleoside will increase the stability of the nucleotide. Examples of substituent groups that can replace one or more hydrogens on the phosphate moiety are alkyl, aryl, steroids, carbohydrates, including sugars, 1,2-diacylglycerol and alcohols. Many are described in R. Jones and N. Bischofberger, *Antiviral Research*, 27 (1995) 1–17. Any of these can be used in combination with the disclosed nucleosides to achieve a desired effect.

In one embodiment, the L-(2' or 3')-A-5-FddC nucleoside is provided as 5'-hydroxyl lipophilic prodrug, i.e., a 5'-ether lipid or a 5'-phosphoether lipid. Nonlimiting examples of U.S. patents that disclose suitable lipophilic substituents that can be covalently incorporated into the nucleoside, preferably at the 5'-OH position of the nucleoside or lipophilic preparations, include U.S. Pat. Nos. 5,149,794 (Sep. 22, 1992, Yatvin et al.); U.S. Pat. No. 5,194,654 (Mar. 16, 1993, Hostetler et al., U.S. Pat. No. 5,223,263 (Jun. 29, 1993, Hostetler et al.); U.S. Pat. No. 5,256,641 (Oct. 26, 1993, Yatvin et al.); U.S. Pat. No. 5,411,947 (May 2, 1995, Hostetler et al.); U.S. Pat. No. 5,463,092 (Oct. 31, 1995, Hostetler et al.); U.S. Pat. No. 5,543,389 (Aug. 6, 1996, Yatvin et al.); U.S. Pat. No. 5,543,390 (Aug. 6, 1996, Yatvin et al.); U.S. Pat. No. 5,543,391 (Aug. 6, 1996, Yatvin et al.); and U.S. Pat. No. 5,554,728 (Sep. 10, 1996; Basava et al.), all of which are incorporated herein by reference.

Foreign patent applications that disclose lipophilic substituents that can be attached to the L-(2' or 3')-A-5-FddC nucleoside derivative of the present invention, or lipophilic preparations, include WO 89/02733, WO 90/00555, WO 91/16920, WO 91/18914, WO 93/00910, WO 94/26273, WO 96/15132, EP 0 350 287, EP 93917054.4, and WO 91/19721.

Additional nonlimiting examples of L-(2' or 3')-A-5-FddC nucleosides are those that contain substituents as described in the following publications. These derivatized nucleosides can be used for the indications described in the text or otherwise as antiviral agents, including as anti-HIV agents. Ho, D. H. W. (1973) Distribution of Kinase and deaminase of 1b-D-arabinofuranosylcytosine in tissues of man and mouse. *Cancer Res*. 33, 2816–2820; Holy, A. (1993) Isopolar phosphorous-modified nucleotide analogues. In: De Clercq (Ed.), Advances in Antiviral Drug Design, Vol. I, JAI Press, pp. 179–231; Hong, C. I., Nechaev, A., and West, C. R. (1979a) Synthesis and antitumor activity of 1b-D-arabinofaranosylcytosine conjugates of cortisol and cortisone. *Biochem. Biophys. Rs. Commun*. 88, 1223–1229; Hong, C. I., Nechaev, A., Kirisits, A. J. Buchheit, D. J. and West, C. R. (1980) Nucleoside conjugates as potential antitumor agents. 3. Synthesis and antitumor activity of 1-(b-D-arabinofuranosyl)cytosine conjugates of corticosteriods and selected lipophilic alcohols. *J Med. Chem.* 28, 171–177; Hostetler, K. Y., Stuhmiller, L. M., Lenting, H. B. M. van den Bosch, H. and Richman, D. D. (1990) Synthesis and antiretroviral activity of phospholipid analogs of azidothyrnidine and other antiviral nucleosides. *J Biol. Chem.* 265, 6112–6117; Hostetler, K. Y., Carson, D. A. and Richman, D. D. (1991); Phosphatidylazidothymidine: mechanism of antiretroviral action in CEM cells. *J Biol. Chem.* 266, 11714–11717; Hostetler, K. Y., Korba, B. Sridhar, C., Gardener, M. (1994a) Antiviral activity of phosphatidyl-dideoxycytidine in hepatitis B-infected cells and enhanced hepatic uptake in mice. *Antiviral Res.* 24, 59–67; Hostetler, K. Y., Richman, D. D., Sridhar, C. N. Felgner, P. L, Felgner, J., Ricci, J., Gardener, M. F. Selleseth, D. W. and Ellis, M.N. (1994b) Phosphatidylazidothymidine and phosphatidyl-ddC: Assessment of uptake in mouse lymphoid tissues and antiviral activities in human immunodeficiency virus-infected cells and in rauscher leukemia virus-infected mice. *Antimicrobial Agents Chemother.* 38,2792–2797; Hunston, R. N., Jones, A. A. McGuigan, C., Walker, R. T., Balzarini, J., and De Clercq, E. (1984) Synthesis and biological properties of some cyclic phosphotriesters derived from 2'-deoxy-5-fluorouridine. J. Med. Chem. 27, 440–444; Ji, Y. H., Moog, C., Schmitt, G., Bischoff, P. and Luu, B. (1990); Monophosphoric acid diesters of 7b-hydroxycholesterol and of pyrimidine nucleosides as potential antitumor agents: synthesis and preliminary evaluation of antitumor activity. *J. Med. Chem.* 33, 2264–2270; Jones, A. S., McGuigan, C., Walker, R. T., Balzarini, J. and DeClercq, E. (1984) Synthesis, properties, and biological activity of some nucleoside cyclic phosphoraridates. J Chem. Soc. Perkin Trans. I, 1, 1471–1474; Juodka, B. A. and Smart, J. (1974) Synthegis of ditribonucleoside a(P→N) amino acid derivatives. Coll. Czech. Chem. Comm. 39, 363–968; Kataoka, S., Imai, J., Yamaji, N., Kato, M., Saito, M., Kawada, T. and Imai, S. (1989) Alkylated cAMP derivatives; selective synthesis and biological activities. *Nucleic Acids Res. Sym. Ser.*, 21, 1–2; Kataoka, S., Uchida, R. and Yamaji, N. (1991) A convenient synthesis of adenosine 3',5'cyclic phosphate (cAMP) benzyl and methyl triesters. *Heterocycles*32, 1351–1356; Kinchington, D., Harvey, J. J., O'C.onnor, T. J., Jones, B.C.N.M., Devine, K. G., Taylor-Robinson, D., Jeffries, D. J. and McGuigan, C. (1992) Comparison of antiviral effects of zidovudine phosphoramidate and phosphorodiamidate derivatives against HIV and ULV in vitro. Antiviral Chem. Chemother. 3, 107–112; Kodama, K., Morozumi, M., Saitoh, K. I., Kuninaka, H., Yoshino, H. and Saneyoshi, M. (1989) Antitumor activity and pharmacology of 1-b-D-arabinofaranosylcytosine -5'-stearylphosphate; an orally active derivative of 1-b-D-arabinofranosylcytosine. Jpn. J. Cancer Res. 80, 679–685; Korty, M. and Engels, J. (1979) The effects of adenosine- and guanosine 3',5'-phosphoric and acid benzyl esters on guinea-pig ventricular myocardium. Naunyn-Schmiedeberg's Arch. Pharmacol. 310, 103–111; Kumar, A., Goe, P. L., Jones, A. S. Walker, R. T. Balzarini, J. and De Clercq, E. (1990) Synthesis and biological evaluation of some cyclic phosphoramidate nucleoside derivatives. *J. Med Chem.* 33, 2368–2375; LeBec, C., and Huynh-Dinh, T. (1991) Synthesis of lipophilic phosphate triester derivatives of 5-fluorouridine and arabinocytidine as anticancer prodrugs. *Tetrahedron Lett.* 32,6553–6556; Lichtenstein, J., Bamer, H. D. and Cohen, S. S. (1960) The metabolism of exogenously supplied nucleotides by *Escherichia coli., J Biol. Chem.* 235, 457–465; Lucthy, J., Von Daeniken, A., Friederich, J. Manthey, B., Zweifel, J., Schlatter, C. and Benn, M. H. (1981) Synthesis and toxicological properties of three naturally occurring cyanoepithioalkanes. Mitt. Geg. Lebensmittelunters. Hyg. 72, 131–133 (*Chem. Abstr.* 95, 127093); McGuigan, C. Tollerfield, S. M. and Riley, P. A. (1989) Synthesis and biological evaluation of sojne phosphate triester derivatives of the anti-viral drug Ara. *Nucleic Acids Res.* 17, 6065–6075; McGuigan, C., Devine, K. G., O'C.onnor, T. J., Galpin, S. A., Jeffries, D. J. and Kinchington, D. (1 990a) Synthesis and evaluation of some novel phosphoramidate derivatives of 3'-azido-3'-deoxythymidine (AZT) as anti-HIV compounds. *Antiviral Chem. Chemother.* 1, 107–113; McGuigan, C., O'Connor, T. J., Nicholls, S. R. Nickson, C. and Kinchington, D. (1990b) Synthesis and anti-HIV activity of some novel substituted dialkyl phosphate derivatives of AZT and ddCyd. *Antiviral Chem. Chemother.* 1, 355–360; McGuigan, C., Nicholls, S. R., O'C.onnor, T. J., and Kinchington, D. (1990c) Synthesis of some novel dialkyl phosphate derivative of 3'-modified nucleosides as potential anti-AIDS drugs. *Antiviral Chem. Chemother.* 1, 25–33; McGuigan, C., Devine, K. G., O'C.onnor, T. J., and Kinchington, D.(1991) Synthesis and anti-HIV activity of some haloalkyl phosphoramidate derivatives of 3'-azido-3'-deoxythymidine (AZT); potent activity of the trichloroethyl methoxyalaninyl compound. *Antiviral Res.* 15, 255–263; Mcruigan, C., Pathirana, R. N., Mahmnood, N., Devine, K. G. and Hay, A. J. (1992) Aryl phosphate derivatives of AZT retain activity against HIV- 1 in cell lines which are resistant to the action of AZT. *Antiviral Res.* 17, 311–321; McGuigan, C., Pathirana, R. N., Choi, S. M., Kinchington, D. and O'Connor, T. J. (1993a) Phosphoramidate derivatives of AZT as inhibitors of HIV; studies on the carboxyl terminus. *Antiviral Chem. Chemother.* 4, 97–101; McGuigan, C., Pathirana, R. N., Balzarini, J. and De Clercq, E. (1993b) Intracellular delivery of bioactive AZT nucleotides by aryl phosphate derivatives of AZT. *J. Med. Chem.* 36, 1048–1052.

The L-(2' or 3')-A-5-FddC nucledside in another embodiment can be provided as a 5' ether lipid or a 5'-phospholipid ether, as disclosed in the following references, which are incorporated by reference herein: Kucera, L. S., N. Lyer, E. Leake, A. Raben, Modest E. J., D. L. W., and C. Piantadosi. 1990. Novel membrane-interactive ether lipid analogs that inhibit infectious HIV-1 production and induce defective virus formation. AIDS Res Hum Retroviruses. 6:491–501; Piantadosi, C., J. Marasco C. J., S. L. morris-Natschke, K. L. Meyer, F. Gumus, J. R. Surles, K. S. Ishaq, L. S. Kucera, N. lyer, C. A. Wallen, S. Piantadosi, and E. J. Modest. 1991-Synthesis and evaluation of novel ether lipid nucleoside conjugates for anti-HIV activity. J Med Chem. 34:1408–1414; Hostetler, K. Y., D. D. Richman, D. A. Carson, L. M. Stuliller, G. M. T. van Wijk, and H. van den Bosch. 1992. Greatly enhanced inhibition of human immunodeficiency virus type 1 replication in CEM and HT4-6C cells by 31 -deoxythymidine diphosphate dimyristoylglycerol, a lipid prodrug of 31-deoxythymidine. Antimicrob Agents Chemother. 36:2025–2029; Hostetler, K. Y., L. M. Stuhmiller, H. B. Lenting, H. van den Bosch, and D. D. Richman. 1990. Synthesis and antiretroviral activity of phospholipid analogs of azidothymidine and other antiviral nucleosides. J. Biol Chem. 265:6112–7.

The question of chair-twist equilibria for the phosphate rings of nucleoside cyclic 3',5'-monophosphates. $^1$HNMR and x-ray crystallographic study of the diasteromers of thymidine phenyl cyclic 3',5'-monophosphate. J. Am. Chem.

Soc. 109,4058–4064; Nerbonne, J. M., Richard, S., Nargeot, J. and Lester, H. A. (1984) New photoactivatable cyclic nucleotides produce intracellular jumps in cyclic AMP and cyclic GMP concentrations. Nature 301, 74–76; Neumann, J. M., Herve, M., Debouzy, J. C., Guerra, F. I., Gouyette, C., Dupraz, B. and Huynh-Dinh, T. (1989) Synthesis and transmembrane transport studies by NMR of a glucosyl phospholipid of thymidine. J. Am. Chem. Soc. 111, 4270–4277; Ohno, R., Tatsumi, N., Hirano, M., Imai, K. Mizoguchi, H., Nakamura, T., Kosaka, M., Takatuski, K., Yamaya, T., Toyama, K., Yoshida, T., Masaoka, T., Hashimoto, S., Ohshima, T., Kimura, I., Yamada, K. and Kimura, J. (1991) Treatment of myelodysplastic syndromes with orally administered 1-b-D-rabinofuranosylcytosine -5'-stearylphosphate. Oncology 48, 451–455. Palomino, E., Kessle, D. and Horwitz, J. P. (1989) A dihydropyridine carrier system for sustained delivery of 2',3'-dideoxynucleosides to the brain. J. Med. Chem. 32, 622–625; Perkins, R. M., Barney, S., Wittrock, R., Clark, P. H., Levin, R. Lambert, D. M., Petteway, S. R., Serafinowska, H. T., Bailey, S. M., Jackson, S., Hamnden, M. R. Ashton, R., Sutton, D., Harvey, J. J. and Brown, A. G. (1993) Activity of BRL47923 and its oral prodrug, SB203657A against a rauscher murine leukemia virus infection in mice. Antiviral Res. 20 (Suppl. I). 84; Piantadosi, C., Marasco, C. J., Jr., Morris-Natschke, S. L., Meyer, K. L., Gumus, F., Surles, J. R., Ishaq, K. S., Kucera, L. S. Iyer, N., Wallen, C. A., Piantadosi, S. and Modest, E. J. (1991) Synthesig and evaluation of novel ether lipid nucleoside conjugates for anti-HIV-1 activity. J. Med. Chem. 34, 1408–1414; Pompon, A., Lefebvre, I., Imbach, J. L., Kahn, S. and Farquhar, D. (1994) Decomposition pathways of the mono- and bis(pivaloyloxymethyl) esters of azidothymidine-5'-monophosphate in cell extract and in tissue culture medium; an application of the on-line ISRP-cleaning' HPLC technique. Antiviral Chem. Chemother. 5, 91–98; Postemark, T. (1974) Cyclic AMP and cyclic GMP. Annu. Rev. Pharmacol. 14, 23–33; Prisbe, E. J., Martin, J. C. M., McGee, D. P. C., Barker, M. F., Smee, D. F. Duke, A. E., Matthews, T. R. and Verheyden, J. P. J. (1986) Synthesis and antiherpes virus activity of phosphate and phosphonate derivatives of 9-[(1,3-dihydroxy-2-propoxy)methyl] guanine. J. Med. Chem. 29, 671–675; Pucch, F., Gosselin, G., Lefebvre, I., Pompon, A., Aubertin, A. M. Dim, A. and Imbach, J. L. (1993) Intracellular delivery of nucleoside monophosphate through a reductase-mediated activation process. Antiviral Res. 22, 155–174; Pugaeva, V. P., Klochkeva, S. I., Mashbits, F. D. and Eizengart, R. S. (1969). Toxicological assessment and health standard ratings for ethylene sulfide in the industrial atmosphere. Gig. Trf. Prof. Zabol. 13, 47–48 (Chem. Abstr. 72, 212); Robins, R. K. (1984) The potential of nucleotide analogs as inhibitors of retroviruses and tumors. Pharm. Res. 11–18; Rosowsky, A., Kim. S. H., Ross and J. Wick, M. M. (1982) Lipophilic 5'-(alkylphosphate) esters of 1-b-D-arabinofiuranosylcytosine and its $N^4$-acyl and 2.2'-anhydro-3'0-acyl derivatives as potential prodrugs. J. Med. Chem. 25, 171–178; Ross, W. (1961) Increased sensitivity of the walker turnout towards aromatic nitrogen mustards carrying basic side chains following glucose pretreatment. Biochem. Pharm. 8, 235–240; Ryu, E. K., Ross, R. J. Matsushita, T., MacCoss, M., Hong, C. I. and West, C. R. (1982). Phospholipid-nucleoside conjugates. 3. Synthesis and preliminary biological evaluation of 1-b-D-arabinofuranosylcytosine 5'-diphosphate[-], 2-diacylglycerols. J. Med. Chem. 25, 1322–1329; Saffhill, R. and Hume, W. J. (1986) The degradation of 5-iododeoxyuridine and 5-bromodeoxyuridine by serum from different sources and its consequences for the use of these compounds for incorporation into DNA. Chem. Biol. Interact. 57, 347–355; Saneyoshi, M., Morozumi, M., Kodama, K., Machida, J., Kuninaka, A. and Yoshino, H. (1980) Synthetic nucleosides and nucleotides. XVI. Synthesis and biological evaluations of a series of 1-b-D-arabinofuranosylcytosine 5'-alkyl or arylphosphates. Chem. Pharm. Bull. 28, 2915–2923; Sastry, J. K., Nehete, P. N., Khan, S., Nowak, B. J., Plunkett, W., Arlinghaus, R. B. and Farquhar, D. (1992) Membrane-permeable dideoxyuridine 5'-monophosphate analogue inhibits human immunodeficiency virus infection. Mol. Pharmacol. 41, 441–445; Shaw, J. P., Jones, R. J. Arimilli, M. N., Louie, M. S., Lee, W. A. and Cundy, K. C. (1994) Oral bioavailability of PMEA from PMEA prodrugs in male Sprague-Dawley rats. 9th Annual AAPS Meeting. San Diego, Calif. (Abstract). Shuto, S., Ueda, S., Imamura, S., Fukukawa, K. Matsuda, A. and Ueda, T. (1987) A facile one-step synthesis of 5'-phosphatidylnucleosides by an enzymatic two-phase reaction. Tetrahedron L Lett. 28, 199–202; Shuto, S., Itoh, H., Ueda, S., Imamura, S., Kukukawa, K., Tsujino, M., Matsuda, A. and Ueda, T. (1988) A facile enzymatic synthesis of 5'-(3-sn-phosphatidyl)nucleosides and their antileukemic activities. Chem. Pharm. Bull. 36, 209–217. One preferred phosphate prodrug group is the S-acyl-2-thioethyl group, also referred to as "SATE."

Figure 2:
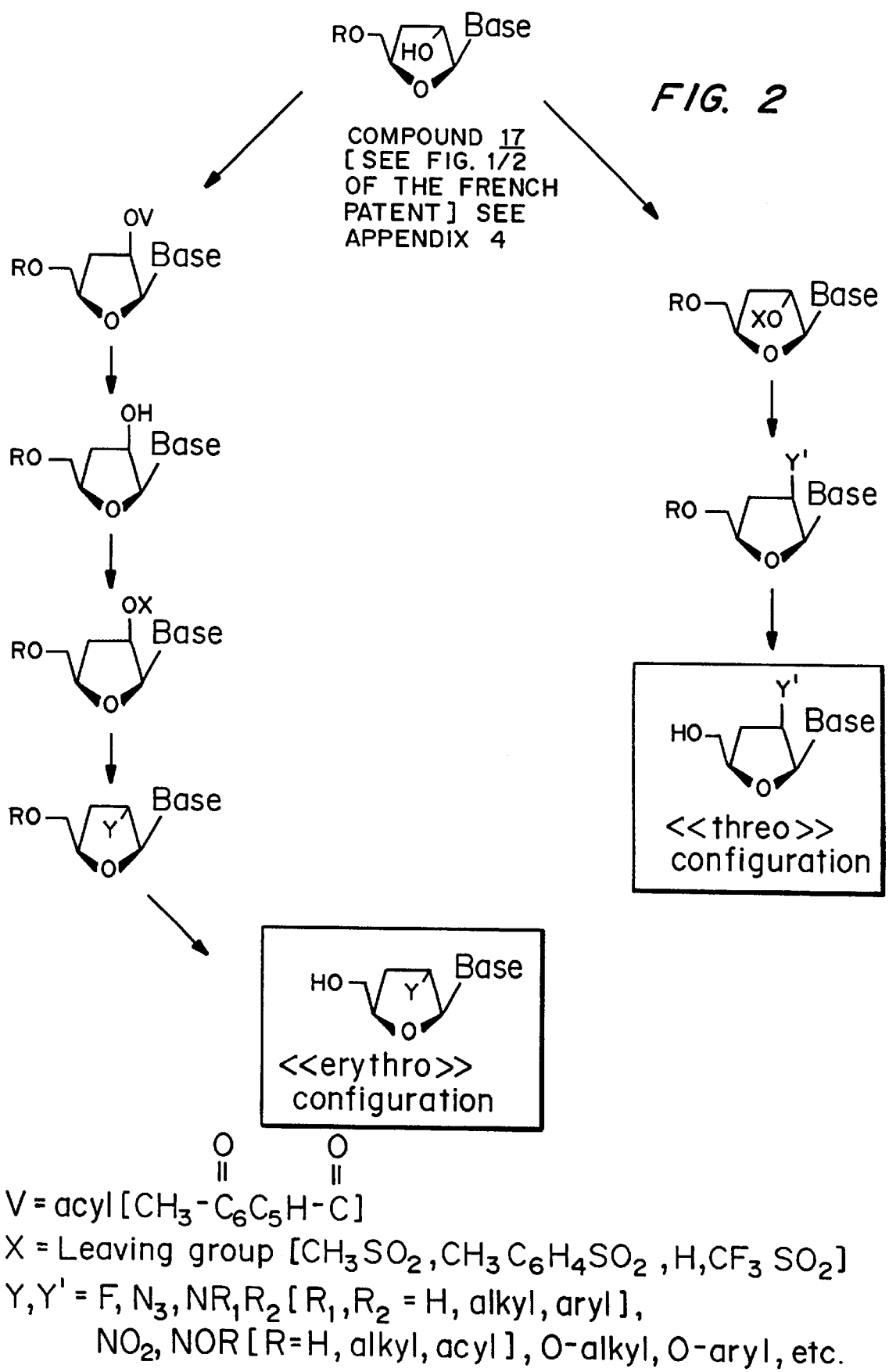
FIG. 2 is an illustration of a general reaction scheme for the stereospecific synthesis of 2'-substituted β-L-dideoxynucleosides.
Figure 3A:
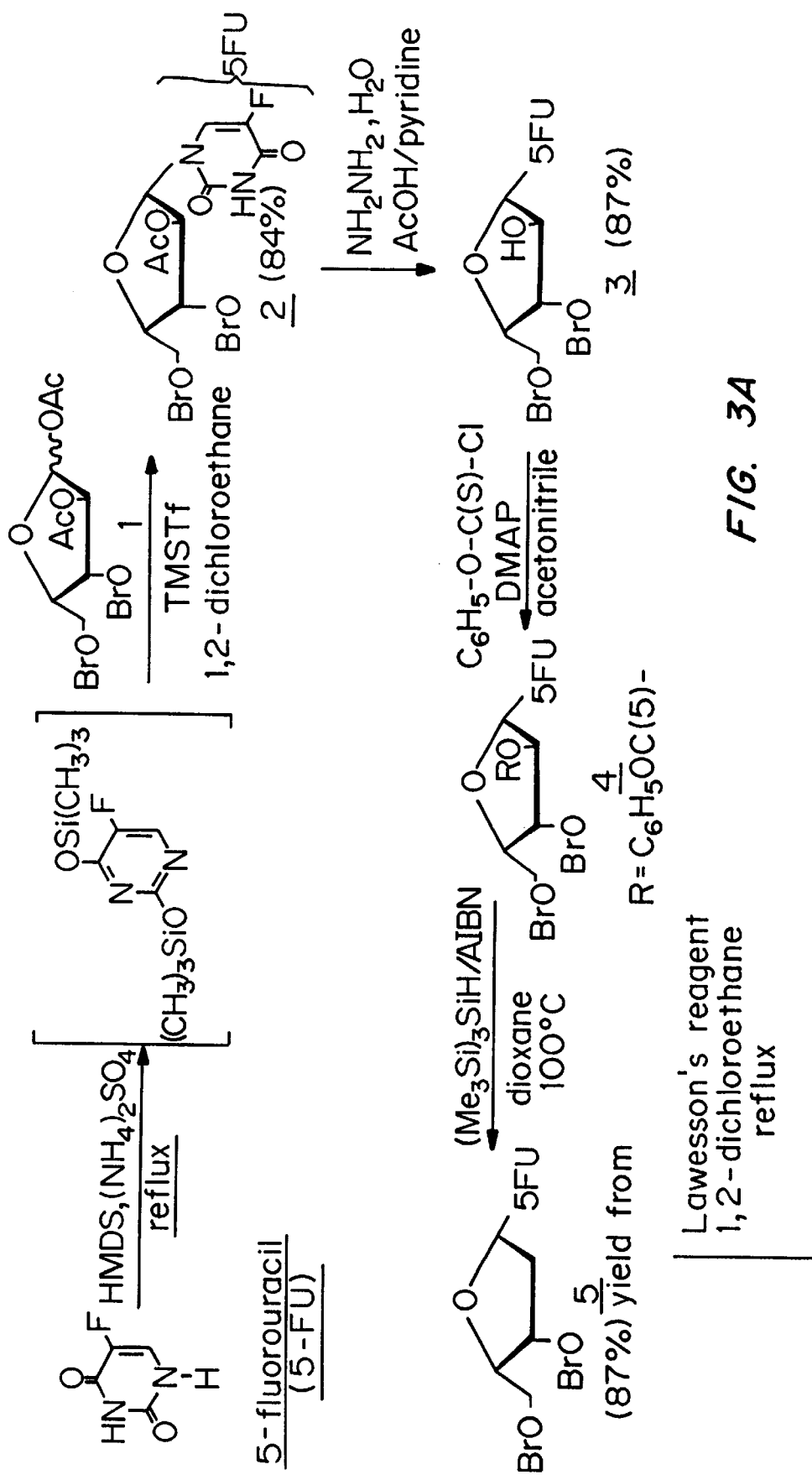
FIG. 3 is an illustration of one process for the preparation of β-L-(3'-azido)-2',3'-dideoxy-5-fluorocytosine (L-3'-A-5-FddC).
Figure 3B:
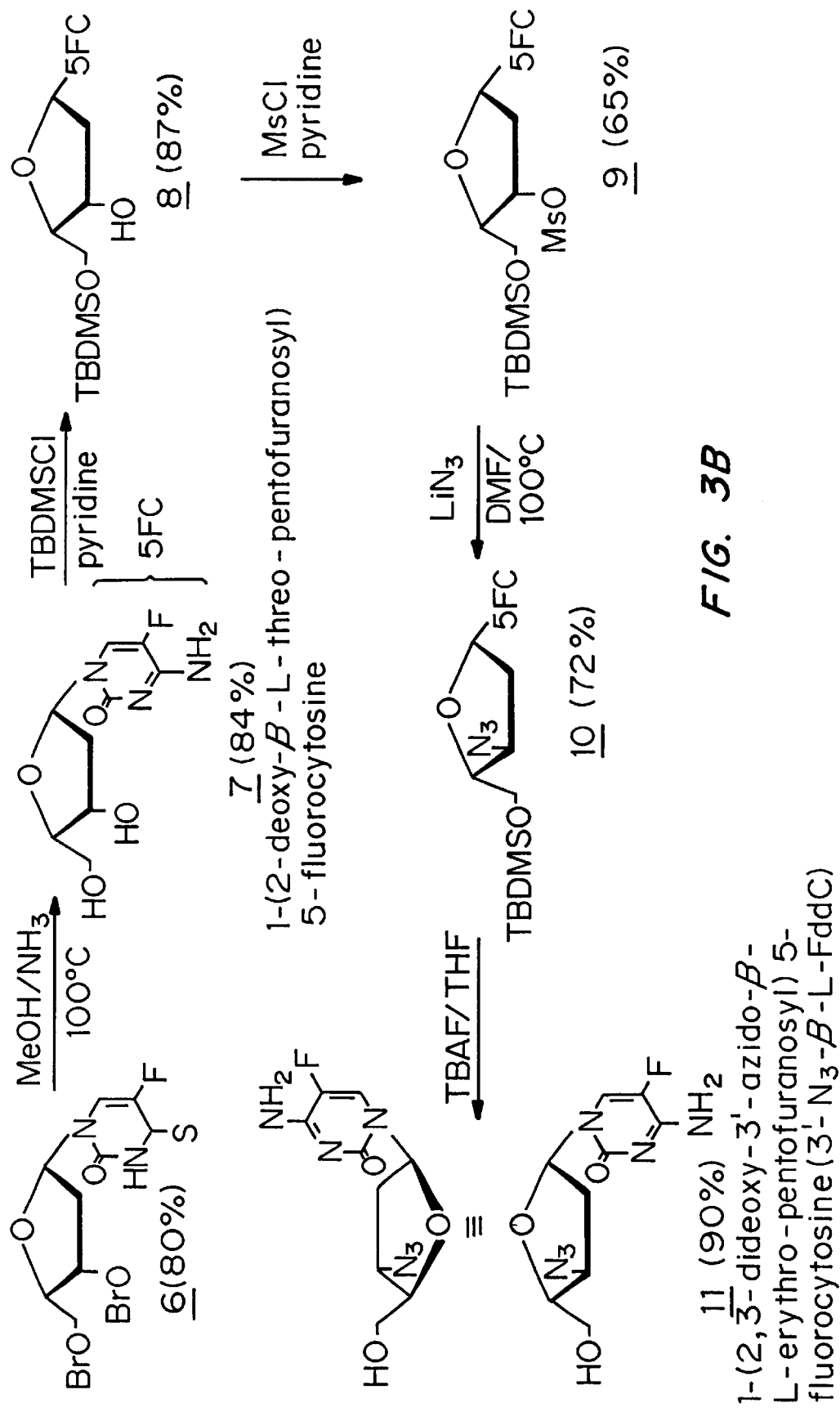
Figure 4A:
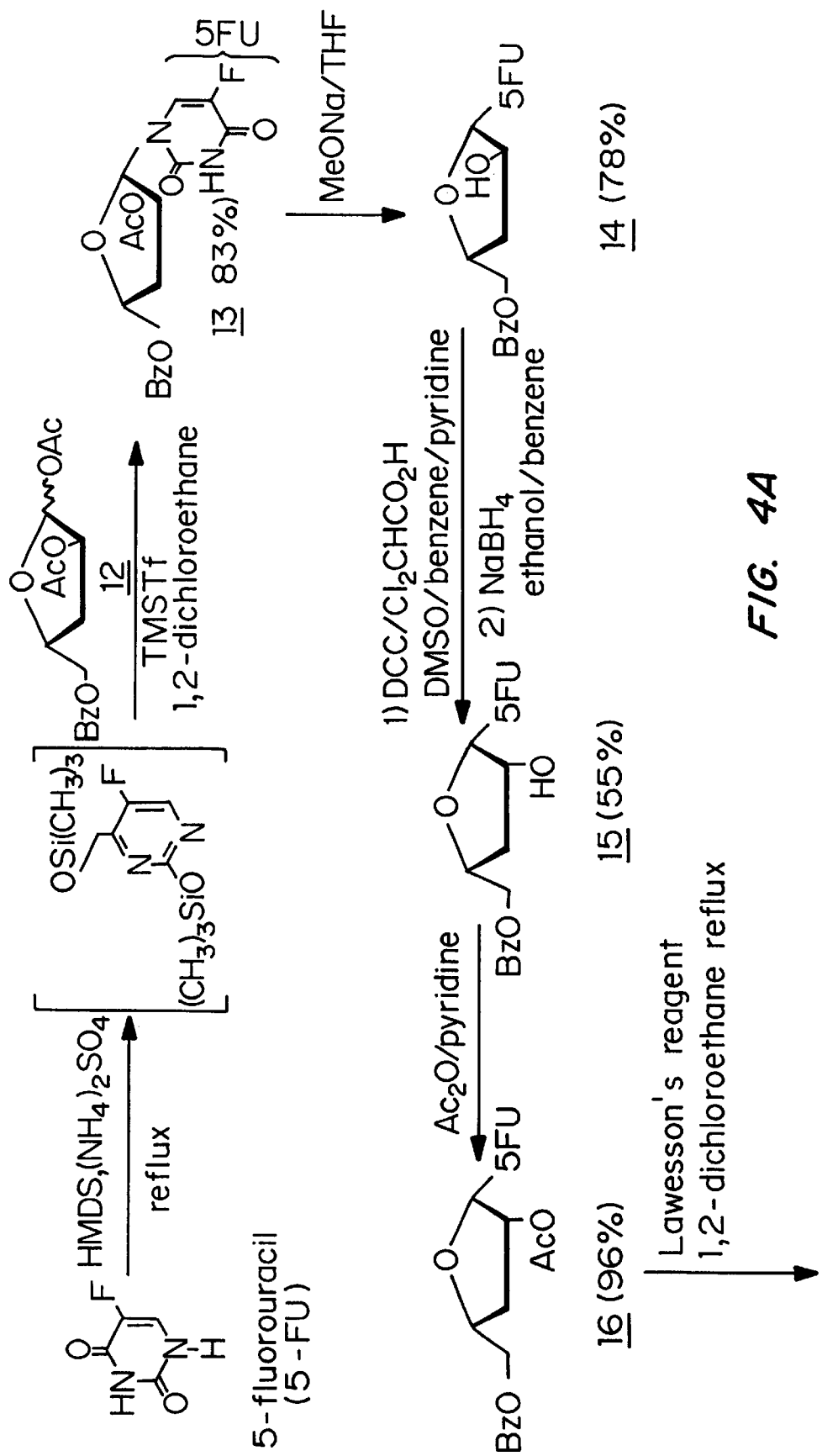
FIG. 4 is an illustration of one process for the preparation of β-L-(2'-azido)-2',3'-dideoxy-5-fiuorocytidine (L-2'-A-5-FddC).
Figure 4B:
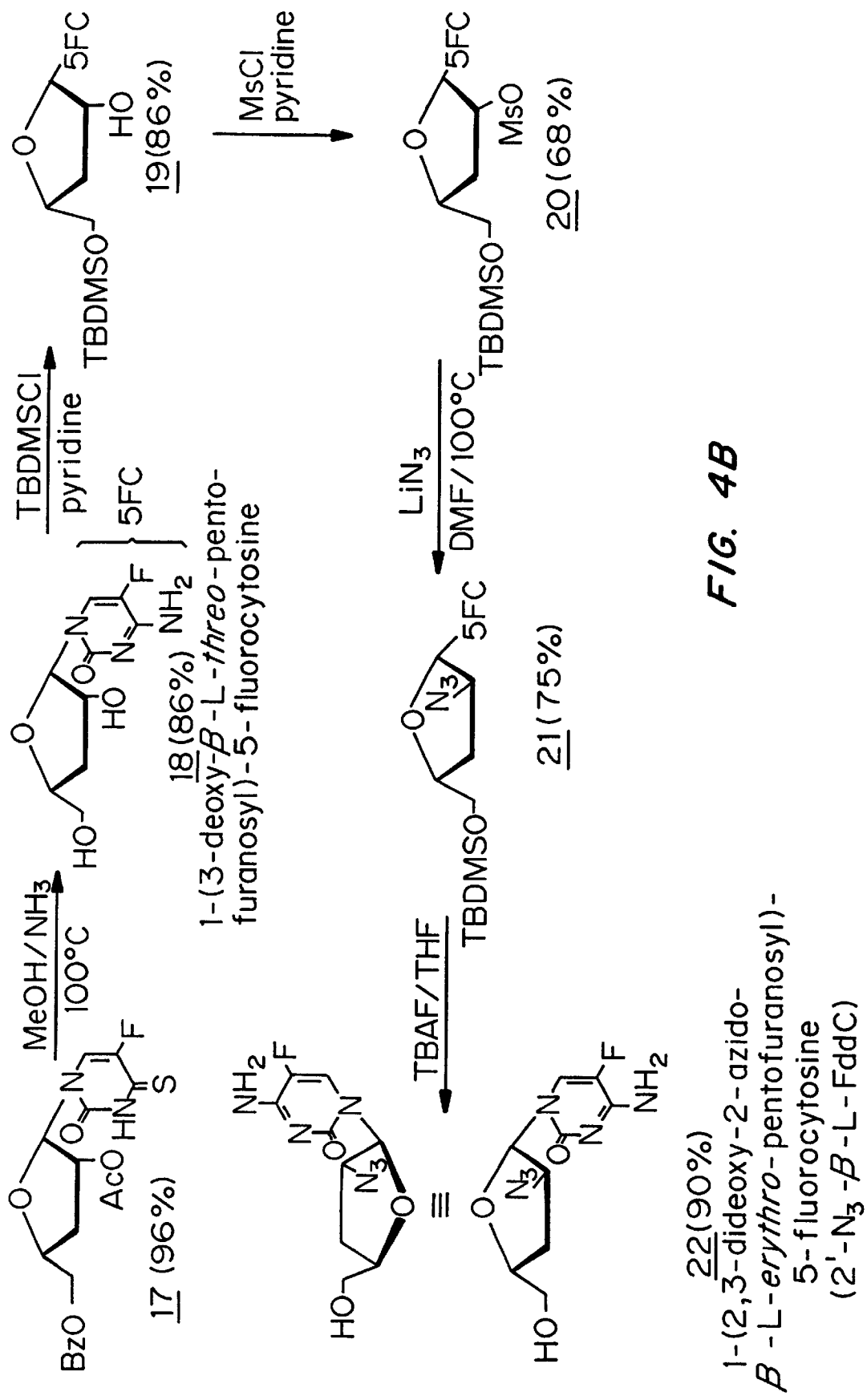

A general process for the stereospecific synthesis of 3'-substituted β-L-dideoxynucleosides is shown in FIG. 1. A general process for the stereospecific synthesis of 2'-substituted β-L-dideoxynucleosides is shown in FIG. 2. A detailed synthesis of β-L-( 3'-azido)-2',3'-dideoxy-5-fluordcytosine is provided in FIG. 3 and in Example 1 below. A detailed synthesis of β-L-(2'-azido)-2',3'-dideoxy-5-fluorocytosine is provided in FIG. 4 and in Example 2 below.

Example 1

Preparation of β-L-(3'-azido)-2',3'-dideoxy-5-fluorocytidine

Melting points were determined in open capillary tubes on a-Gallenkamp MFB-595–010 M apparatus and are uncorrected. The UV absorption spectra were recorded on an Uvikon 931 (KONTRON) spectrophotometer in ethanol. $^1$H-NMR spectra were run at room temperature in DMSO-$d_6$ with a Bruker AC 250 or 400 spectrometer. Chemical shifts are given in ppm, DMSO-$d_5$ being set at 2.49 ppm as reference. Deuterium exchange, decoupling experiments or 2D-COSY were performed in order to confirm proton assignments. Signal multiplicities are represented by s (singlet), d (doublet), dd (doublet of doublets), t (triplet), q (quadruplet), br (broad), m (multiplet). All J-values are in Hz. FAB mass spectra were recorded in the positive-(FAB>0) or negative (FAB<0) ion mode on a JEOL DX 300 mass spectrometer. The matrix was 3-nitrobenzyl alcohol (NBA) or a mixture (50:50, v/v) of glycerol and thioglycerol (GT). Specific rotations were measured on a Perkin-Elmer 241 spectropolarimeter (path length 1 cm) and are given in units of $10^{-1}$ deg $cm^2$ $g^{-1}$. Elemental analysis were carred out by the "Service de Microanalyses du CNRS, Division de Vernaison" (France). Analyses indicated by the symbols of the elements or functions were within ±0.4% of theoretical values. Thin layer chromatography was performed on pre-coated aluminium sheets of Silica Gel 60 $F_{254}$ (Merck, Art. 5554), visualization of products being accomplished by UV absorbency followed by charring with 10% ethanolic sulfric acid and heating. Column chromatography was carried out on Silica Gel 60 (Merck, Art. 9385) at atmospheric pressure.

A suspension of 5-fluorouracil (5.0 g, 38.4 mmol) was treated with hexamethyldisilazane (HMDS, 260 mnL) and a catalytic amount of ammonium sulfate during 18 h under reflux. After cooling to room temperature, the mixture was evaporated under reduced pressure, and the residue obtained as a colorless oil was diluted with anhydrous 1,2-dichloroethane (260 mL). To the resulting solution was added 1,2-di-O-acetyl-3,5-di-O-benzoyl-L-xylofuranose 1 (11.3 g, 25.6 mmol) [Ref.: Gosselin, G.; Bergogne, M.-C.; Imbach, J.-L., "Synthesis and Antiviral Evaluation of β-L-Xylofuranosyl Nucleosides of the Five Naturally Occurring Nucleic Acid Bages", *Journal of heterocyclzc Chemisty*, 1993, 30 (October-November), 1229–1233] in anhydrous 1,2-dichloroethane (130 mL), followed by addition of trimethylsilyl trifluoromethanesulfonate (TMSTf, 9.3 mL, 51.15 mmol). The solution was stirred for 6 h at room temperature under argon atmosphere, then diluted with chloroform (1 L), washed with the same volume of a saturated aqueous sodium hydrogen carbonate solution and finally with water (2×800 mL). The organic phase was dried over sodium sulphate, then evaporated under reduced pressure. The resulting crude material was purified by silica gel column chromatography [eluent: stepwise gradient of methanol (0–4%) in methylene chloride] to give 2 (11.0 g, 84% yield) as a white foam; mp=96–98° C.; UV (ethanol): $\lambda_{max}$= 228 nm ($\epsilon$=25900) 266 nm ($\epsilon$=9000), $\lambda_{min}$=250 nm ($\epsilon$=7200); $^1$H-NMR (DMSO-d$_6$): δ 11.1 (br s, 1H, NH), 8.05 (1H, H-6, $J_{6-F5}$=6.8 Hz), 7.9–7.4 (m, 10H, 2 C$_6$H$_5$CO), 5.99 (d, 1H, H-1', $J_{1'-2'}$=3.1 Hz), 5.74 (dd, 1H, H-3', $J_{3'-2'}$=4.2 Hz and $J_{3'-4'}$=2.3 Hz), 5.54 (t, 1H, H-2', $J_{2'-1'}$=$J_{2'-3'}$=2,9 Hz), 4.8–4.6 (m, 3H, H-4', H-5'and H-5"); MS: FAB>0 (matrix GT) m/z 513 (M+H)$^+$, 383 (S)$^+$, 105 (C$_6$H$_5$CO)$^+$; FAB<0 (matrix GT) m/z 511 (M–H)$^-$, 469 (M-CH$_3$CO)$^-$, 129 (B)$^-$, 121 (C$_6$H$_5$CO$_2$)$^-$; $[\alpha]_D^{20}$ =–91 (c, 0.88 DMSO); Anal C$_{25}$H$_{21}$FN$_2$O$_9$(C, H, N, F).

1-(3,5-Di-O-benzoyl-β-L-xylofuranosyl)-5-fluorouracil 3

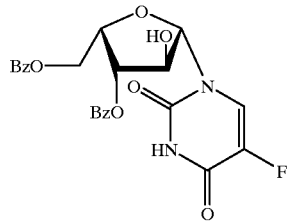

Hydrazine hydrate (2.80 mL, 57.4 mmol) was added to a solution of 1-(2-O-acetyl-3,5-di-o-benzoyl-β-L-xylofuranosyl)-5-fluorouracil 2 (9.80 g, 19.1 mmol) in acetic acid (35 mL) and pyridine (150 mL). The resulting solution was stirred overnight at room temperature. Acetone (50 mL) was added and the mixture was stirred during 2 h. The reaction mixture was concentrated to a small volume and partitioned between ethyl acetate (200 mL) and water (200 mL). Layers were separated and the organic phase was washed with a saturated aqueous sodium hydrogen carbonate solution (2×200 mL), and finally with water (2×200 mL). The organic phase was dried over sodium sulphate, then evaporated under reduced pressure. The resulting residue was purified by silica gel column chromatography [eluent: stepwise gradient of methanol (0–5%) in methylene chloride] to give pure 3 (7.82 g, 87%), which was crystallized from methylene chloride; mp=93–97° C.; UV (ethanol): $\lambda_{max}$=227 nm ($\epsilon$=22800) 267 nm ($\epsilon$=8200), $\lambda_{min}$= 249 nm ($\epsilon$=5900); $^1$H-NMR (DMSO-d$_6$): δ 11.9 (br s, 1H, NH), 8.06 (d, 1H, H-6, $J_{6-F5}$=6.9 Hz), 8.0–7.4 (m, 10H, 2 C$_6$H$_5$CO), 6.35 (d, 1H, OH-2', $J_{OH-2'}$=3.8 Hz), 5.77 (d, 1H, H-1', $J_{1'-2'}$=3.3 Hz), 5.43 (dd, 1H, H-3', $J_{3'-2'}$=3.1 Hz and $J_{3'-4'}$=1.9 Hz) 4.8–4.6 (m, 3H, H-4', H-5'and H-5"), 4.43 (t, 1H, H-2', J=2.3 Hz); MS: FAB>0 (matrix GT) m/z 941 (2M+H)$^+$, 471 (M+H)$^+$, 341 (S)$^{30}$, 131 (BH$_2$)$^+$, 105 (C$_6$H$_5$CO)$^+$; FAB<0 (matrix GT) m/z 939 (2M–H)$^-$, 469 (M–H)$^-$, 129 (B)$^-$, 121 (C$_6$H$_5$CO$_2$)$^-$; $[\alpha]_D^{20}$=–110 (C, 1.55 DMSO).

1-(2-Deoxy-3,5-di-o-benzoyl-β-L-threo-pentofuranosyl)-5-fluorouracil 5

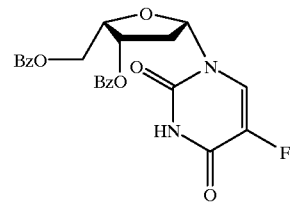

To a solution of 1-(3,5-di-O-benzoyl-β-L-xylofuranosyl)-5-fluorouracil 3 (15.4 g, 32.7 mmol) in anhydrous acetonitrile (650 mL) were added O-phenyl chlorothionoformate (6.80 mL, 49.1 mmol) and 4-dimethylaminopyridine (DMAP, 12.0 g, 98.2 mmol). The resulting solution was stirred at room temperature under argon during 1 h and then evaporated under reduced pressure. The residue was dissolved in methylene chloride (350 mL) and the organic solution was successively washed with water (2×250 mL), with an ice-cold 0.5 N hydrochloric acid (250 mL) and with water (2×250 mL), dried over sodium sulphate and evaporated under reduced pressure. The crude material 4 was co-evaporated several times with anhydrous dioxane and dissolved in this solvent (265 mL). To the resulting solution were added under argon tris(trimethylsilyl)silane hydride (12,1 mL, 39.3 mmol) and α,α'-azoisobutyronitrile (AIBN, 1.74 g, 10.8 mmol). The reaction mixture was heated and stirred at 100° C. for 2.5 h under argon, then cooled to room temperature and evaporated under reduced pressure. The residue was purified by silica gel column chromatography [eluent: stepwise gradient of methanol (0–2%) in chloroform] to give pure 5 (13.0 g, 87%), which was crystallized from a diethyl ether/methanol mixture; mp=182–184° C.; UV (ethanol):$\lambda_{max}$229 nm ($\epsilon$=25800), 269 nm ($\epsilon$=9300), $\lambda_{min}$=251 nm ($\epsilon$=6500); $^1$H-NMR (DMSO-d$_6$): δ 11.8 (br s, 1H, NH), 8.05 (d, 1H, H-6, $J_{6-F5}$=7.0 Hz), 8.0–7.4 (m, 10H, 2 C$_6$H$_5$CO), 6.15 (d, 1H, H-1, $J_{1'-2'}$=7.4 Hz), 5.68 (t, 1H, H-3', $J_{3'-2'}$=4.2 Hz), 4.8–4.6 (m, 2H, H-5' and H"-5), 4.6 (m, 1H, H-4'), 3.0–2.8 (m, 1H, H-2'), 2.5–2.3 (d, 1H, H-2", J=14.8 Hz); MS: FAB>0 (matrix GT) m/z 455 (M+H)$^+$, 325 (S)$^+$, 131 (BH$_2$)$^+$, 105 (C$_6$H$_5$CO)$^+$; PAB<0 (matrix GT) m/z 452 (M–H)$^-$, 129 (B)$^-$; $[\alpha]_D^{20}$=–125 (c 1.05 DMSO); Anal C$_{23}$H$_{19}$FN$_2$O$_7$(C, H, N, F).

1-(2-Deoxy-3,5-di-o-benzoyl-β-L-threo-pentofuranosyl)-4-thio-5-fluorouracil

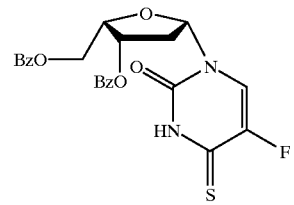

Lawesson's reagent (3.1 g, 7.70 mmol) was added under argon to a solution of 5 (5.0 g, 11.0 mmol) in anhydrous 1,2-dichloroethane (200 mL) and the reaction mixture was stirred overnight under reflux. The solvent was then evaporated under reduced pressure and the residue was purified by silica gel column chromatography [eluent: stepwise gradient of methanol (0–2%) in chloroform] to give the 4-thio intermediate 6 (80% yield) as a yellow foam; mp=178–179° C.; UV (ethanol): $\lambda_{max}$=230 nm ($\epsilon$=24900), 273 nm ($\epsilon$=6900), 333 nm ($\epsilon$=19200), $\lambda_{min}$=258 nm ($\epsilon$=5900), 289 nm ($\epsilon$=5300); $^1$H-NMR (DMSO-d$_6$): δ 13.1 (br s, 1H, NH), 8.10 (d, 1H, H-6, $J_{6\text{-}F5}$=4,6 Hz), 8.1–7.4 (m, 10H, 2 C$_6$H$_5$CO), 6.09 (d, 1H, H-1', $J_{1'\text{-}2'}$=7.3 Hz), 5.68 (t, 1H, H-3', $J_{3'\text{-}2'}$=$J_{3'\text{-}4'}$=4.1 Hz), 4.9–4.8 (m, 2H, H-5' and H-5"), 4.7 (m, 1H, H-4'), 2.9 (m, 1H, H-2'), 2.5 (m, 1H, H-2"); MS: FAB>0 (matrix GT) m/z 941 (2M+H)$^+$, 471 (M+H)$^+$, 325 (S)$^+$, 147 (BH$_2$)$^+$, 105 (C$_6$H$_5$CO)$^+$; FAB<0 (matrix GT) m/z 469 (M–H)$^-$, 145 (B)$^-$, 121 (C$_6$H$_5$CO$_2$)$^-$; $[\alpha]_D^{20}$=–271 (c, 0,90 DMSO); Anal C$_{23}$H$_{19}$FN$_2$O$_6$S (C, H, N, F).

1-(2-Deoxy-β-L-threo-pentofuranosyl)-5-fluorocytosine 7

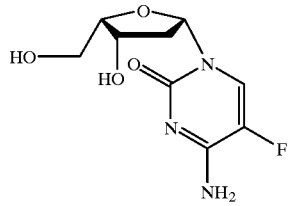

A solution of this 4-thio intermediate 6 (1.0 g, 2.13 mmol) in methanolic ammonia (Previously saturated at –10° C. and tightly stopped) (60 mL) was heated at 100° C. in a stainless-steel bomb for 3 h and then cooled to 0° C. The solution was evaporated to dryness under reduced pressure and the residue co-evaporated several times with methanol. The crude material was dissolved in water and the resulting solution was washed four times with methylene chloride. The aqueous layer was evaporated under reduced pressure and the residue was purified by silica gel column chromatography [eluent: stepwise gradient of methanol (3–20%) in methylene chloride]. Finally, the appropriate fractions were evaporated under reduced pressure, diluted with methanol and filtered through a unit Millex HV-4 (0,45 μm, Millipore) to provide 0.44 g of 7 (84% yield) which was crystallized from an ethyl acetate/methanol mixture; mp=199–201° C.; UV (ethanol): $\lambda_{max}$=226 nm ($\epsilon$=7700), 281 nm ($\epsilon$=8500), $\lambda_{min}$=262 nm ($\epsilon$=6300); $^1$H-NMR (DMSO-d$_6$): δ 7.99 (d, 1H, H-6, $J_{6\text{-}F5}$=7.4 Hz), 7.7–7.4 (br d, 2H, NH$_2$), 5.98 (d, 1H, H-1', $J_{1'\text{-}2'}$=8.1 Hz), 5.25 (d, 1H, OH-3',$J_{OH\text{-}3}$3.4 Hz), 4.71 (t, 1H, OH-5', $J_{OH\text{-}5'}$=$J_{OH\text{-}5"}$=5.6 Hz), 4.2 (m, 1H, H-3'), 3.8–3.6 (m, 3H, H-4', H-5' and H-5"), 2.5 (m, 1H, H-2'), 1.8 (m, 1H, H-2"); MS: FAB>0 (matrix GT) m/z 491 (2M+H)$^+$, 246 (M+H)$^+$, 130 (BH$_2$)$^+$; FAB<0 (matrix GT) m/z 489 (2M–H)$^-$, 244 (M–H)$^-$, 128 (B)$^-$; $[\alpha]_D^{20}$=–21 (c, 0.92 DMSO); Anal C$_9$H$_{12}$FN$_3$O$_4$ (C, H, N, F).

1-(2-Deoxy-5-O-t-butyldimethylsilyl-β-L-threo-pentofuranosyl)-5-fluorocytosine 8

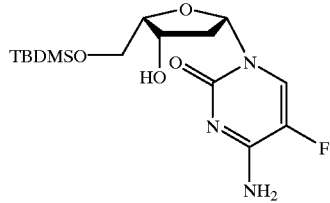

To a solution of 7 (1.69 g, 6.89 mmol) in dry pyridine (35 mL) was added dropwise under argon atmosphere t-butyldimethylsilyl chloride (1.35 g, 8.96 mmol) and the mixture was stirred for 5 h at room temperature. Then the mixture was poured onto a saturated aqueous sodium hydrogen carbonate solution (100 mL) and extracted with chloroform (3×150 mL). Combined extracts were washed with water (2×200 mL) and then dried over sodium sulphate and evaporated under reduced pressure. The residue was purified by silica gel column chromatography [eluent : stepwise gradient of methanol (2–10%) in methylene chloride] to give pure 8 (2.94 g, 87%), as a white solid: mp 177–179° C.; UV (ethanol): $\lambda_{max}$241 nm ($\epsilon$9900), 282 nm ($\epsilon$10000), $\lambda_{min}$226 nm ($\epsilon$8200), 263 nm ($\epsilon$7600); $^1$H NMR (DMSO-d$_6$): δ 7.95 (d, 1H, H-6, $J_{6\text{-}F5}$=7.3 Hz), 7.8–7.3 (br d, 2H, NH$_2$), 6.00 (dd, 1H, H-1', $J_{1'\text{-}2'}$=6.1 Hz and $J_{1'\text{-}2"}$=1.9 Hz), 5.3 (br s, 1H, OH-3'), 4.2 (br s, 1H, H-3'), 3.9–3.7 (m, 3H, H-4', H-5' and H-5"), 2.5 (m, 1H, H-2'), 1.81 (br d, 1H, H-2", J=14.6 Hz), 0.86 s, 9H, (CH$_3$)$_3$C—Si), 0.05 (s, 6H, (CH$_3$)$_2$Si); MS (matrix GT): FAB>0 m/z 719 (2M+H)$^+$, 360 (M+H)$^+$, 130 (BH$_2$)$^+$, 115 (TBDMS)$^+$; FAB<0 m/z 717 (2M–H)$^-$, 5 358 (M–H)$^-$, 128 (B)$^-$; $[\alpha]_D^{20}$=–23 (c, 0.96 DMSO).

1-(2-Deoxy-3-O-mesyl-5-O-t-butyldimethylsilyl-β-L-threo-pento furanosyl)-5-fluorocytosine 9

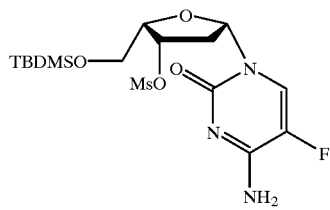

A suspension of 8 (0.70 g, 1.96 mmol) in dry pyridine (30 mL) was stirred under argon and cooled to 0° C. Methanesulfonyl chloride (MsCl, 0.46 mL, 5.88 mmol) was added dropwise and the reaction mixture stirred at 0° C. for 5 h. Then the mixture was poured onto ice/water (100 mL) and extracted with chloroform (3×100 mL). Combined extracts were washed with a 5% aqueous sodium hydrogen carbonate solution (100 mL), with water (2×100 mL), dried over sodium sulphate and evaporated under reduced pressure. The resulting residue was purified by silica gel column chromatography [eluent: stepwise gradient of methanol (8–12%) in toluene] to give pure 9 (0.56 g, 65%) as a white solid: mp 83–84 ° C.; UV (ethanol): $\lambda_{max}$242 nm ($\epsilon$8500), 282 nm ($\epsilon$8800), $\lambda_{min}$225 nm ($\epsilon$6400), 264 nm ($\epsilon$6300); $^1$H NMR (DMSO-d$_6$): δ 7.8–7.3 (br d, 2H, NH$_2$), 7.60 (d, 1H, H-6, J$_{6-F5}$=7.0 Hz), 5.93 (dd, 1H, H-1', J$_{1'-2'}$=4.5 Hz and J$_{1'-2''}$=2.0 Hz), 5.2 (m, 1H, H-3'), 4.1 (m, 1H, H-4'), 3.9–3.7 (m, 2H, H-5' and H-5''), 3.17 (s, 3H, CH$_3$SO$_2$), 2.7 (m, 1H, H-2'), 2.1 (m, 1H, H-2 ''), 0.99 (s, 9H, (CH$_3$)$_3$C—Si), 0.05 (s, 6H, (CH$_3$)$_2$Si); MS (matrix GT): FAB>0 m/z 875 (2M+ H)$^+$, 438 (M+H)$^+$, 342 (M-CH$_3$SO$_3$)$^+$, 130 (BH$_2$)$^+$; FAB<0 m/z 873 (2M–H)$^-$, 436 (M–H)$^-$, 128 (B)$^-$, 95 (CH$_3$SO$_3$)$^-$; [α]$_D^{20}$=–28 (c, 0.96 DMSO).

1-(2,3-Dideoxy-3-azido-5-O-t-butyldimethylsilyl-β-L-erythro-pentofuranosyl)-5-fluorocytosine 10

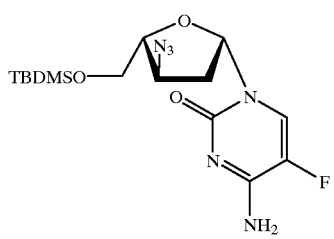

To a solution of 9 (520 mg, 1.19 mmol) in anhydrous dimethylformamide (12 mL) was added lithium azide moistened with 10% methanol (300 mg, 5.31 mmol). The reaction mixture was stirred at 100° C. dunng 2.5 h, and then cooled to room temperature, poured onto ice/water (200 mL) and extracted with chloroform (3×100 mL). Combined extracts were washed with saturated aqueous sodium hydrogen carbonate solution (2×100 mL), with water (5×100 mL), and then dried over sodium sulphate and evaporated under reduced pressure. The residue was purified by silica gel column chromatography [eluent: methanol (4%) in chloroform] to give pure 10 (327 mg, 72%), which was crystallized from a diethyl ether/methanol mixture: mp 146–147° C.; UV (ethanol): λ$_{max}$243 nm (ε8700), 283 nm (ε8400), λ$_{min}$226 nm (ε7200), 264 nm (ε6700); $^1$H NMR (DMSO-d$_6$): δ 7.90 (d, 1H, H-6, J$_{6-F5}$=7.0 Hz) 7.8–7.5 (br d, 2H, NH$_2$) 6.0 (m, 1H, H-1'), 4.3 (m, 1H, H-3'), 3.9–3.7 (m, 3H, H-4', H-5' and H''-5), 2.4–2.2 (m, 2H, H-2' and H-2''), 0.87 (s, 9H, (CH$_3$)C—Si), 0.05 (s, 6H, (CH$_3$)$_2$Si); MS (matrix GT): FAB>0 m/z 769 (2M+H)$^+$, 385 (M+H)$^+$, 130 (BH$_2$)$^+$; FAB<0 m/z 383 (M–H)$^-$; [α]$_D^{20}$=–67 (c, 0.96 DMSO).

1-(2,3-Dideoxy-3-azido-ε-L-erythro-pentofuranosyl)-5-fluorocytosine 11 (3'-N$_3$-β-L-5-FddC)

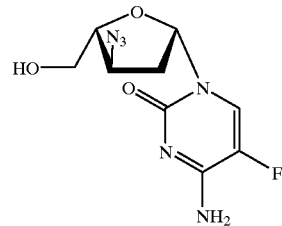

A 1 M solution of tetrabutylammonium trifluoride in tetrahydrofurane (TBAF/THF, 1.53 mL, 1.53 mmol) was added to a solution of 10 (295 mg, 0.67 mmol) in anhydrous THF (4 mL). The resulting mixture was stirred at room temperature for 1.5 h and evaporated under reduced pressure. The residue was purified by silica gel column chromatography [eluent: stepwise gradient of methanol (4–8%) in chloroform]. Finally, the appropriate fractions were evaporated under reduced pressure, diluted with methanol and filtered through a unit Millex HV-4 (0,45 μm, Millipore) to give pure 11 (199 mg, 96%), which was crystallized from ethanol: mp 188–189° C. (lit: mp 164–166° C. for tihe D-enantiomer); UV (ethanol): λ$_{max}$243 nm (ε8700), 283 nm (ε8100), λmin226 nm (ε7100), 264 nm (ε6500); $^1$H NMR (DMSO-d$_6$): δ 8.08 (d, 1H, H-6, J$_{6-F5}$=7.3 Hz), 7.8–7.5 (br d, 2H, NH2), 6.0 (m, 1H, H-1'), 5.3 (br s, 1H, OH-5'), 4.4 (m, 1H, H-3'), 3.8 (m, 1H, H-4'), 3.7–3.5 (m, 2H, H-5' and H-5''), (m, 2H, H-2' and H-2''); MS (matrix GT): FAB>0 m/z 811 (3M+H)$^+$, 725 (2M+2G+H)$^+$, 633 (2M+G+H)$^+$, 541 (2M+H)$^+$, 363 (M+G+H)$^+$, 271 (M+H)$^+$, 142 (S)$^+$, 130 (BH$_2$)$^+$; FAB<0 m/z 647 (2M+T–H)$^-$, 539 (2M–H), 377 (M+T–H)$^-$, 269 (M–H)$^-$, 128 (B)$^-$; [α]$_D^{20}$=–31 (c, 0.90 DMSO); Anal. (C$_9$H$_{11}$FN$_6$O$_3$) C, H, N, F.

|  |  | Analytical data | | | | | | | |
| --- | --- | --- | --- | --- | --- | --- | --- | --- | --- |
|  |  | Anal Calculated | | | | Anal Found | | | |
| Compound | Formula | C | H | N | F | C | H | N | F |
| 2 | C$_{25}$H$_{21}$FN$_2$O$_9$ | 58.59 | 4.13 | 5.47 | 3.71 | 58.33 | 4.25 | 4.24 | 3.49 |
| 5 | C$_{23}$H$_{19}$FN$_2$O$_7$ | 60.79 | 4.21 | 6.17 | 4.18 | 61.22 | 4.26 | 6.18 | 3.90 |
| 6 | C$_{23}$H$_{19}$FN$_2$O$_6$S | 58.71 | 4.07 | 5.96 | 4.04 | 58.25 | 4.10 | 5.91 | 4.00 |
| 7 | C$_9$H$_{12}$FN$_3$O$_4$ | 44.08 | 4.87 | 17.17 | 7.75 | 43.87 | 5.13 | 16.81 | 7.42 |
| 11 | C$_9$H$_{11}$FN$_6$O$_3$ | 40.00 | 4.10 | 31.10 | 7.03 | 40.35 | 3.83 | 31.38 | 7.12 |

Example 2

Preparation of β-L(2'-azido)-2',3'-dideoxy-5-fluorocytidine

Genral procedures and instrumentation used have been described in Example 1 in the Experimental protocols part of the synthesis of the 3' isomer (3'-N$_3$-β-L-FddC).

1-(2-O-acetyl-3-deoxy-5-O-benxoyl-β-L-erythro-pentofuranosyl)-5-flurourcil 13

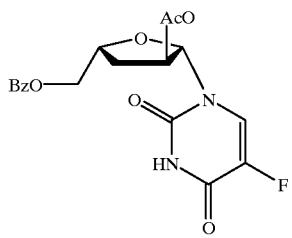

A spension of 5-fluorouracil (5.15 g, 39.6 mmrrol) was treated with hexamethyldisilazane (HMDS, 257 mL) and a catalytic amount of ammnonium sulfate during 18 h undre reflux. After cooling to room temperature, the mixture was evaporated under reduced presssure, and the residue obtained as a colourless oil was diluted with anhydrous 1,2-dichloroethane (290 mL). To the resulting solution was added 1,2-di-O-acetyl-3-deoxy-5-O-benzoyl-L-erythro-pentofuranose 12 (8.5 g, 26.4 mmol) [Ref.: Mathé, C., *Ph. D. Dissertation*, Universitéde Montpellier II -Sciences et Techniques du Languedoc, Montpellier (France), Sep. 13, 1994; Gosselin, G.; Mathé, C.; Bergogne, M.-C.; Aubertin, A. M.; Kim, A.; Sommadossi, J. P.; Schinazi, R. F.; Imbach, J. L., "2'- and/or 3'-deoxy-β-L-pentofuranosyl nucleoside derivatives: stereospecific synthesis and antiviral activities," *Nucleosides & Nucleotides*, 1994, 14 (3–5), 611–617] in anhydrous 1,2-dichloroethane (120 mL), followed by addition of trimethylsilyl trifluoromethanesulfonate (TMSTf, 9.6 mL, 52.8 mmol). The solution was stirred for 5 h at room temperature under argon atmosphere, then diluted with chloroform (200 mL), washed with the same volume of a saturated aqueous sodium hydrogen carbonate solution and finally with water (2×300 mL). The organic phase was dried over sodium sulphate, then evaporated under reduced pressure. The resulting crude material was purified by silica gel column chromatography [eluent: stepwise gradient of methanol (0–6%) in methylene chloride] to give pure 13 (8.59 g, 83%), which was crystallized from toluene: mp 65–68° C.; UV (ethanol): $\lambda_{max}$228 nm (ε11200) 268 nm (ε14000), $\lambda_{min}$242 nm (ε7800); $^1$H NMR (DMSO-d$_6$): δ 11.9 (br s, 1H, NH), 8.0–7.5 (m, 6H, C$_6$H$_5$CO and H-6), 5.8 (m, 1H, H-1'), 5.3 (m, 1H, H-2'), 4.6–4.5 (m, 3H, H-4', H-5' and H-5"), 2.4–2.3 (m, 1H, H-3'), 2.1–2.0 (m, 4H, H-3" and CH$_3$CO); MS (matrix GT): FAB>0 m/z 393 (M+H)$^+$, 263 (S)$^+$, 105 (C$_6$H$_5$CO)$^+$; FAB<0 m/z 391 (M–H)$^-$, 331 (M-[CH$_3$CO$_2$H]-H)$hu$ –, 129 (B)$^-$, 121 (C$_6$H$_5$CO$_2$)$^-$; $[α]_D^{20}$=–8 (c, 1.00 DMSO); Anal. (C$_{18}$H$_{17}$FN$_2$O$_7$; ⅔ C$_7$H$_8$) C, H, N, F.

1-(3-Deoxy-5-O-benzoyl-β-L-erythro-pentofuranosyl)-5-fluorouracil 14

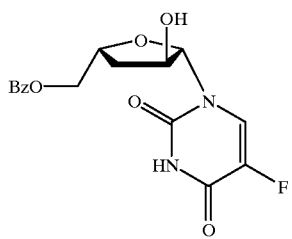

To a solution of 13 (5.90 g, 15.0 mmol) in tetrahydrofurane (THF, 175 mL), was added sodium methoxide (2.84 g, 52.6 mmol). The resulting suspension was stirred at room temperature during 5 h and then neutralized by addition of Dowex 50 WX2 (H$^+$ form). The resin was filtered and washed with wann methanol, and the combined filtrates were evaporated to dryness. Column chromatography of the residue on silica gel [eluent: stepwise gradient of methanol (0–8%) in methylene chloride] afforded 14 (4.11 g, 78%), which was crystallized from a methylene chloride/methanol mixture: mp 154–156° C.; UV (ethanol): $\lambda_{max}$226 nm (ε23000), 268 nm (ε16000), $\lambda^{min}$246 nm (ε8900); $^1$H NMR (DMSO-d$_6$): δ 11.8 (br s, 1H, NH), 8.0–7.5 (m, 6H, C$_6$H$_5$CO and H-6), 5.6 (br s, 2H, H-1' and OH-2'), 4.5 (m, 3H, H-4', H-5' and H-5'), 4.3 (m, 1H, H-2'), 2.1–2.0 (m, 1H, H-3'), 1.9 (m, 1H, H-3"); MS (matrix GT): FAB>0 m/z 701 (2M+H)$^+$, 351 (M+H)$^+$, 221 (S)$^+$, 131 (BH$_2$)$^+$, 105 (C$_6$H$_5$CO)$^+$; FAB<0 m/z 1049 (3M–H)$^-$, 699 (2M–H)$^-$, 441 (M+G–H)$^-$, 349 (M–H)$^-$, 129 (B)$^-$, 121 (C$_6$H$_5$CO$_2$)$^-$; $[α]_D^{20}$=–3 (c, 1.04 DMSO); Anal. (C$_{16}$H$_{15}$FN$_2$O$_6$) C, H, N, F 1-(3-Deoxy-5-O-benzoyl-β-L-threo-pentofuranosyl)-5-fluorouracil 15

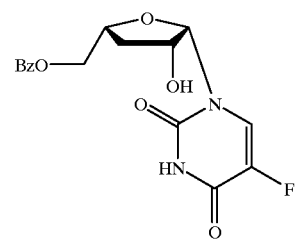

Dicyclohexylcarbodiimide (DCC, 3.53 g, 17.1 mmol) and dichloroacetic acid (0.235 mL, 2.56 mmol) were added to a solution of 14 (2.00 g, 5.71 mmol) in anhydrous benzene (50 mL), DMSO (35 mL) and pyridine (0.46 mL). The resulting solution was stirred at room temperature under argon during 4 h and diluted with ethyl acetate (300 mL). Oxalic acid (1.54 g, 17.1 mmol) dissolved in methanol (4.6 mL) was added and the reaction mixture was stirred at room temperature during 1 h and then filtered to eliminate precipitated dicyclohexylurea (DCU). The filtrate was washed with brine (3×300 mL), with a saturated aqueous sodium hydrogen carbonate solution (2□ 300 mL) and finally with water (3×200 mL) before being dried over sodium sulphate and evaporated under reduced pressure. The resulting residue was co-evaporated several times with absolute ethanol and dissolved in a mixture of absolute ethanol (31 mL) and anhydrous benzene (15 mL). The resulting solution as then cooled to 0° C. and sodium borohydride (NaBH$_4$, 0.32 g, 8.56 mmol) was added. The reaction mixture was stirred at room temperature under argon during 1 h and diluted with ethyl acetate (300 mL) filtered. The filtrate was washed with a saturated aqueous sodium chloride solution (3×300 mL) and with water (2□ 200 mL) before being dried over sodium sulphate and evaporated under reduced pressure. The resulting residue was purified by silica gel column chromatography [eluent: stepwise gradient of methanol (0–6%) in chloroform] to. give pure 15 (1.10 g, 55%), as a white foam: mp 171–172□C; UV (ethanol): $\lambda_{max}$228 nm (ε14700) 270 nm (ε9100), $\lambda_{min}$248 nm (ε5000); $^1$H NMR (DMSO-d$_6$): δ11.8 (br s, 1H, NH), 8.0–7.5 (m, 6H, C$_6$H$_5$CO and H-6), 5.90 (dd, 1H, H-1', J$_{1'-2'}$=4.1 Hz and J$_{1'-F5}$=1.8 Hz), 5,5 (br s, 1H, OH-2'), 4.7 (br q, 1H, H-4'J=11.7 Hz and J=7.0 Hz), 4.4–4.3 (m, 3H, H-2', H-5' and H-5"), 2.4 (m, 1H, H-3'), 1.9–1.8 (m, 1H, H-3"); MS (maxtrix GT): FAB>0 m/z 701 (2M+H)$^+$, 351 (M+H)$^+$, 221 (S)$^+$, 131 (BH$_2$)$^+$, 105 (C$_6$H$_5$CO)$^+$; FAB<0 m/z 1049 (3M–H)$^-$, 699 (2M–H)$^-$, 349 (M–H)$^-$; 129 (B)$^-$, 121 (C$_6$H$_5$CO$_2$)$^-$; $[α]_D^{20}$=–101 (c, 0.70 DMSO).

1-(2-O-acetyl-3deoxy-5-O-benzoyl-β-L-threo-pentofuranosyl)-5-fluorouracil 16

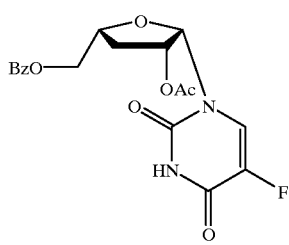

Acetic anhydride (0.88 mL, 9.28 mmol) was added under argon to a solution of 15 (2.50 g, 7.14 mmol) in dry pyridine (50 mL) and the resulting mnixture was stirred at room temperature for 22 h. Then, ethanol was added and the solvents were evaporated under reduced pressure. The residue was purified by silica gel column chromatography [eluent: stepwise gradient of methanol (0–2%) in methylene chloride] to give pure 16 (2.69 g, 96%) as a white foam; mp=68–70° C. (foam); UV (ethanol): $\lambda_{max}$239 nm ($\epsilon$=15000) 267 nm ($\epsilon$=8800), $\lambda_{min}$=248 nm ($\epsilon$=5600); $^1$H NMR (DMSO-d$_6$): δ ppm 11.9 (br s, 1H, NH), 8.1–7.5 (m, 6H, C$_6$H$_5$CO and H-6), 6.10 (d, 1H, H-1', $J_{1'-2'}$=4.3 Hz), 5.4 (m, 1H, H-2'), 4.6–4.4 (m, 3H, H-4', H-5' and H-5"), 2.6 (m, 1H, H-3'), 2.03 (m, 1H, H-3"), 1,86 (s, 3H, CH$_3$CO); MS (matrix GT): FAB>0 m/z 785 (2M+H)$^+$, 393 (M+H)$^+$, 263 (S)$^+$, 131 (BH$_2$)$^+$, 105 (C$_6$H$_5$CO)$^+$, 43 (CH$_3$CO)$^+$; FAB<0 m/z 391 (M–H)$^-$, 129 (B)$^-$, 121 (C$_6$H$_5$CO$_2$)$^-$, 59 (CH$_3$CO$_2$)$^-$; $[\alpha]_D^{20}$=–81 (c, 0.95 DMSO).

1-(2-acetyl-3-deoxy-5-O-benzoyl-β-L-threo-pentofuranosyl)-4-thio-5-fluorouracil 17

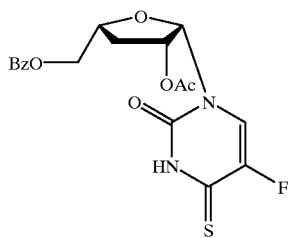

Lawesson's reagent (1.9 g, 4.69 mmol) was added under argon to a solution of 16 (2.63 g, 6.70 mmol) in anhydrous 1,2-dichloroethane (165 mL) and the reaction mixture was stirred overnight under reflux. The solvent was then evaporated under reduced pressure and the residue was purified by silica gel column chromatography [eluent: stepwise gradient of methanol (0–3%) in methylene chloride] to give the 4-thio derivative 17 (2.65 g, 96% yield) as a yellow foam; mp=78–79° C. (foam); UV (ethanol): $\lambda_{max}$=230 nm ($\epsilon$=15900) 334 nm ($\epsilon$=15600), $\lambda_{min}$=288 nm ($\epsilon$=3200); $^1$H NMR (DMSO-d$_6$): δ ppm 13.2 (br s, 1H, NH), 8.1–7.5 (m, 6H, C$_6$H$_5$CO and H-6), 6.08 (d, 1H, H-1', $J_{1'-2'}$=4.3 Hz), 5.4 (m, 1H, H-2') 4.7–4.4 (m, 3H, H-4', H-5' and H-5"), 2.6 (m, 1H, H-3'), 2.0 (m, 1H, H-3"), 1.84 (s, 3H, CH$_3$CO); MS (matrix GT): FAB>0 m/z 409 (M+H)$^+$, 263 (S)$^+$, 147 (BH$_2$)$^+$, 105 (C$_6$H$_5$CO)$^+$, 43 (CH$_3$CO)$^+$; FAB<0 m/z 407 (M–H)$^-$, 145 (B)$^-$, 121 (C$_6$H$_5$CO$_2$)$^-$, 59 (CH$_3$C$_2$)$^-$; $[\alpha]_D^{20}$=–155 (c, 1.00 DMSO).

1-(3-Deoxy-β-L-threo-pentofuranosyl)-5-fluorocytosine 18

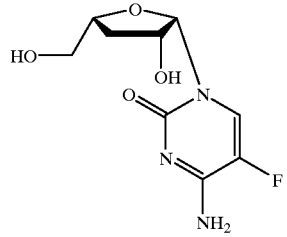

A solution of the 4-thio derivative 17 (0.86 g, 2.19 mmol) in methanolic ammonia (previously saturated at –10° C. and tightly stopped) (44 mL) was heated at 100° C. in a stainless-steel bomb for 3 h and then cooled to 0° C. The solution was evaporated to dryness under reduced pressure and the residue co-evaporated several times with methanol. The crude material was dissolved in water and the resulting solution was washed four times with methylene chloride. The aqueous layer was evaporated under reduced pressure and the residue was purified by silica gel column chromatography [eluent: stepwise gradient of methanol (3–12%) in chloroform]. Finally, the appropriate fractions were evaporated under reduced pressure, diluted with methanol and filtered through a unit Millex HV-4 (0.45 μm, Millipore) to provide 0.46 g of 18 (86% yield) which was crystallized from a methylene/methanol mixture; mp=137–138° C.; UV (ethanol): $\lambda_{max}$=240 nm ($\epsilon$=8300) 284 nm ($\epsilon$=8100), $\lambda_{min}$=226 nm ($\epsilon$=7300) 263 nm ($\epsilon$=5500); $^1$H NMR (DMSO-d$_6$): δ ppm 8.34 (d, 1H, H-6, $J_{6-F5}$=7.5 Hz), 7.7–7.4 (br pd, 2H, NH$_2$), 5.83 (dd, 1H, H-1', $J_{1'-2'}$=4.4 Hz, $J_{1'-F5}$=1.9 Hz), 5.22 (d, 1H, OH-2', $J_{OH-2'}$=5.1 Hz), 5.15 (t, 1H, OH-5', $J_{OH-5'}$=$J_{OH-5"}$4.8 Hz), 4.3 (m, 1H, H-2'), 4.0 (m, 1H, H-4'), 3.6–3.5 (m, 2H, H-5' and H-5") 2.2 (m, 1H, H-3'), 1.7 (m1H, H-3"); MS (matrix GT): FAB>0 m/z 491 (2M+H)$^+$, 246 (M+H)$^+$, 130 (BH$_2$)$^+$; FAB<0 m/z 244 (M–H)$^-$, 128 (B)$^-$; $[\alpha]_D^{20}$=–135 (c, 0.89 DMSO). Elemental analysis, C$_9$H$_{12}$FN$_3$O$_4$, ½ H$_2$O; Calc. C=42.52; H=5.15; N=16.53; F=7.47; Found: C=43.16; H=5.32; N=16.97; F=6.92.

1-(3-Deoxy-5-O-t-butyldimethylsilyl-β-L-threo-pentofuranosyl)-5-fluorocytosine 19

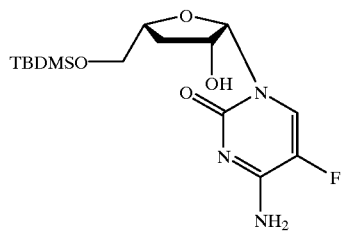

To a solution of 8 (1.38 g, 5.63 mmol) in dry pyridine (30 mL) was added dropwise under argon atmosphere t-butyldimethylsilyl chloride (1.10 g, 7.32 mmol) and the mixture was stirred for 10 h at room temperature. Then the mixture was poured onto a saturated aqueous sodium hydrogen carbonate solution (100 mL) and extracted with chloroform (3×150 mL). Combined extracts were washed with water (2×200 mL) and then dried over sodium sulphate and evaporated under reduced pressure. The residue was purified by silica gel column chromatography [eluent: stepwise gradient of methanol (2–10%) in methylene chloride] to give pure 19 (1.74 g, 86% yield) as a white solid: mp 202–204° C.; UV (ethanol): $\lambda_{max}$241 nm ($\epsilon$7800), 284 nm ($\epsilon$7800), $\lambda_{min}$226 nm ($\epsilon$6600), 263 nm ($\epsilon$5400); $^1$H NMR (DMSO-d$_6$): δ 7.77 (d, 1H, H-6, $J_{6-F5}$=7.1 Hz), 7.7–7.3 (br d, 2H, NH$_2$), 6.88 (dd, 1H, H-1', $J_{1'-2'}$=4.9 Hz and $J_{1'-F5}$=1.9 Hz), 5.24 (d, 1H, OH-3', $J_{OH-3'}$=4.6 Hz), 4.4 (m, 1H, H-2'), 4.0 (m, 1H, H-4'), 3.8–3.7 (m, 2H, H-5' and H-5"), 2.2 (m, 1H, H-3'), 1.7 (m, 1H, H-3"), 0.84 s, 9H, (CH$_3$)$_3$C—Si), 0.06(s, 6H, (CH$_3$)$_2$Si); MS (matrix GT): FAB>0 m/z 1437 (4M+H)$^+$, 1078 (3M+H), 719 (2M+H)$^+$, 360 (M+H)$^+$, 231 (S)$^+$ 130 (BH$_2$)$^+$, 115 (TBDMS)$^+$; FAB<0 m/z 1076 (3M–H)$^-$, 717 (2M–H)$^-$, 358 (M–H)$^-$, 128 (B)$^-$; $[\alpha]_D^{20}$=–107 (c, 0.88 DMSO).

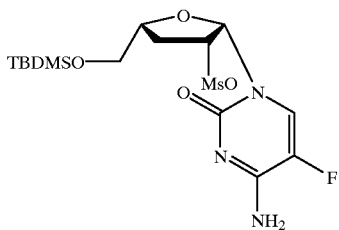

A suspension of 19 (1.70 g, 4.73 mmol) in dry pyridine (80 mL) was stirred under argon and cooled to 0° C. Methanesulfonyl chloride (MsCl, 1.21 mL, 15.6 mmol) was added dropwise and the reaction mixture stirred at 0° C. for 5 h. Then the mixture was poured onto ice/water (300 mL) amd extracted with chloroform (3×300 mL). Combined extracts were washed with a 5% aqueous sodium hydrogen corbonate solution (300 mL), with water (2×300 mL) and then dried over sodium sulphate and evaporated under reduced pressure. The resulting residue was purified by silica gel column chromatography [eluent: stepwise gradient of methanol (8–12%) in toluene] to give pure 20 (1.41 g, 68% yield) as a white solid: mp 75–76° C.; UV (ethanol): $\lambda_{max}$243 nnm ($\epsilon$8100), 282 nm ($\epsilon$7300), $\lambda_{min}$225 nm ($\epsilon$6000), 265 nm ($\epsilon$6000); $^1$H NMR (DMSO-d$_6$): δ 7.9 (br d, 2H, NH$_2$), 7.85 (d, 1H, H-6, $J_{6-F5}$=7.0 Hz), 6.08 (dd, 1H, H-1', $J_{1'-2'}$=5.2 Hz and $J_{1'-F5}$=1.6 Hz), 5.4 (m, 1H, H-2'), 4.1 (m, 1H, H-4'), 3.9 (m, 1H, H-5'), 3.7 (m, 1H, H-5"), 3.11 (s, 3H, CH$_3$SO$_2$), 2.47 (m, 1H, H-3'), 2.0 (m, 1H, H-2"), 0.85 (s, 9H, (CH$_3$)$_3$C—Si), 0.05 (s, 6H, (CH$_3$)$_2$Si); MS (matrix Gt): FAB>0 m/z 1312 (3M+H)$^+$, 875 (2M+H)$^+$, 438 (M+H)$^+$, 309 (S)$^+$, 130 (BH$_2$)$^+$; FAB<0 m/z 1310 (2M–H)$^-$, 873 (2M–H)$^-$, 436 (M–H)$^-$, 128 (B)$^-$, 95 (CH$_3$SO$_3$)$^-$; $[\alpha]_D^{20}$=–84 (c, 0.84 DMSO).

1-(2,3-Dideoxy-2-azido-5-O-t-butyldimethylsilyl-,β-L-erythropentofuranosyl)-5-fluorocytosine 21

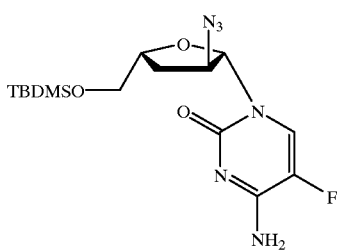

To a solution of 20 (442 mg, 1.01 mmol) in anhydrous dilmethylformamide (12 mL) was added lithium azide moistened with 10% methanol (265 mg, 4.87 mmol). The reaction mixture was stirred at 100° C. during 2.5 h, and then cooled to room temperature, poured onto ice/water (200 mL) and extracted with chloroform (3×100 mL). Combined extracts were washed with a saturated aqueous sodium hydrogen carbonate solution (2×100 mL), with water (5×100 mL) and then dried over sodium sulphate and evaporated under reduced pressure. The residue was purified by silica gel column chromatography [eluent : methanol (4%) in chloroform] to give pure 21 (291 mg, 75% yield) as a white solid: mp 147–148° C.; UV (ethanol): $\lambda_{max}$242 nm ($\epsilon$7700), 283 nm ($\epsilon$7400), $\lambda_{min}$226 inm ($\epsilon$6600), 264 nm ($\epsilon$5800); $^1$H NMR (DMSO-d$_6$): δ 8.05 (d, 1H, H-6, $J_{6-F5}$=7.0 Hz), 7.9–7.4 (br d, 2H, NH$_2$), 5.7 (br s, 1H, H-1'), 4.37 (d, 1H-2', $J_{2'-3'}$=5.5 Hz), 4.3 (m, 1H, H-4'), 4. (m, 1H, H-5'), 3.7 (m, 1H, H-5"), 2.0 (m, 1H, H-3'), 1.8 (m, 1H, H-3"), 0.88 (s, 9H, (CH$_3$)$_3$C—Si), 0.05 (s, 6H, (CH$_3$)$_2$Si); MS (matrix GT): FAB>0 m/z 769 (2M+H)$^+$, 385 (M+H)$^+$, 130 (BH$_2$)$^+$; FAB<0 m/z 1151 (3M–H)$^-$, 767 (2M–H)$^-$, 383 (M–H)$^-$, 128 (B)$^-$; $[\alpha]_D^{20}$=+25 (c, 0.95 DMSO).

1-(2,3-Dideoxy-2-azido-β-L-erythro-pentofuranosyl)-5-fluorocytosin 22 (2'-N$_3$-β-L-5-FddC)

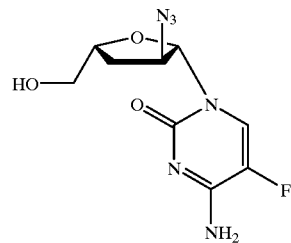

A 1 M solution of tetrabutylammonium trifluoride in tetrahydrofurane (TBAF/THF, 1.90 mL, 1.90 mmol) was added to a solution of 21 (480 mg, 1.25 mmol) in anhydrous THF (8 mL). mL). The resulting mixture was stirred at room temperature for 1.5 h and evaporated under reduced pressure. The residue was purified by silica gel column chromatography [eluent: stepwise gradient of methanol (4–8%) in chloroform]. Finally, the appropriate fractions were evaporated under reduce pressure, diluted with methanol and filter through a unit Millex HV-4 (0.45 μm, Millipore) to give pure 22 (304 mg, 90% yield), which was crystallized from ethanol: mp 219–221° C.; UV (ethanol): $\lambda_{max}$241 nm ($\epsilon$7700), 284 nm ($\epsilon$7300), $\lambda_{min}$225 nm ($\epsilon$6500), 263 nm ($\epsilon$5400), 1H NMR (DMSO-d$_6$): δ 6 8.31 (d, 1H, H-6, $J_{6-F5}$=7.4 Hz), 7.9–7.4 (br d, 2H, NH$_2$), 5.65 (m, 1H, H-1'), 5.32 (brs, 1H OH-5'), 4.35 (d, 1H, H-2', $J_{2'-3'}$=5.6 Hz), 4.2 (m, 1, H-4'), 3.8 (m, 1H, H-5'), 3.6 (m, 1H, H-5"), 2.1 (m, 1H, H-3'), 1.8 (m, 1H, H-2"); MS (matreix GT): GAB>0 m/z 541 (2M+H)$^+$, 363 (M+G+H)$^+$, 271 (M+H)$^+$, 130 (BH$_2$)$^+$; FAB<0 m/z 539 (2M–H)$^-$, 269 (M–H)$^-$, 128 (B)$^-$; $[\alpha]_D^{20}$=+ 29 (c, 0.85 DMSO); Anal. (C$_9$H$_{11}$FN$_6$O$_3$) C, H, N, F.

| | | Analytical data | | | | | | | |
|---|---|---|---|---|---|---|---|---|---|
| | | Anal. calculated | | | | Anal. found | | | |
| Compd | Formula | C | H | N | F | C | H | N | F |
| 13 | $C_{18}H_{17}FN_2O_7$, $2/3C_7H_8$ | 59.99 | 4.96 | 6.18 | 4.19 | 59.60 | 4.96 | 6.02 | 3.76 |
| 14 | $C_{16}H_{15}FN_2O_6$ | 54.86 | 4.32 | 8.00 | 5.42 | 54.75 | 4.16 | 7.78 | 5.49 |
| 22 | $C_9H_{11}FN_6O_3$ | 40.00 | 4.10 | 31.10 | 7.03 | 40.07 | 4.16 | 31.10 | 6.99 |

Anti-HIV Activity of the Active Compounds

Antiviral composition can be scerrned in vito for inhibition of HIV by various experimental techiques. One such technique involves measuring the inhibition of viral replication in human peripheral blood mononuclear (PBM) cells. The amount of virus produced is determined by measuring the quantity of virus-coded reverse transcriptase (RT), an enzyme found in retroviruses, that is present in the cell culture medium.

Three-day-old phytohemagglutinin-stimulated PBM cells ($10^6$ cells/ml) from hepatitis B and HIV-1 seronegative healthy donors were infected with HIV-1 (strain LAV) at a concentration of about 100 times the 50% tissue culture infectious done (TICD 50) per ml and cultured in the presence and absence of various concentrations of antiviral compounds.

Approximately one hour after infection, the medium, with the compound to be tested (2 times the final concentration in medium) or without compound, was added to the flasks (5 ml; final volume 10 ml). AZT was used as a positive control. The cells were exposed to the virus (about $2 \times 10^5$ dpm/ml, as determined by reverse transcriptase assay ) and then placed in a $CO_2$ incubator. HIV-1 (strain LAV) was obtained from the Centers for Disease Control, Altanta, Georgia. The method used for culturing the PBM cell, harvesting the virus and determining the reverse transcriptase activity were those decribed by McDougal et al. (*J. Immum. Meth.* 76, 171–181, 1985) and Spira et al., (*J. Clin. Meth.* 25, 97–99, 1987), except that fungizone was not included in the medium (see Schinazi, et al., *Antimicrob. Agents chemother.* 32, 1784–1787 (1988); *Antimicrob. Agents Chemother.*, 34: 1061–1067 (1990)).

On day 6, the cells and supernatant were transferred to a 15 ml tube and centrifuged at about 900 g for 10 minutes. Five ml of supernatant were removed and the virus was concentrated by centrifugation at 40,000 rpm for 30 minutes (Beckman 70.1 Ti rotor). The solubilized virus pellet was processed for determination of the levels of reverse transcriptase. Results are expressed in dpm/ml of sampled supernatant. Virus from smaller volumes of supernatant (1 ml) can also be concentrated by centrifugation prior to solubilization and determination of reverse transcriptase levels.

The median effective ($EC_{50}$) concentration was determined by the median effect method (*Antimicrob. Agents Chemother.* 30, 491–498 (1986). Briefly, the percent inhibition of virus, as determined from measurements of reverse transcriptase, is plotted versus the micromolar concentration of compound. The $EC_{50}$ is the concentration of compound at which ther is a 50% inhibition of viral growth.

Mitogen stimulated uninfected human PBM cells ($3.8 \times 10^5$ cells/ml) were cultured in the presence and absence of drug under similar conditions as those used for the antiviral assay described above. The cells were counted after six days using a hemacytometer and the trypan blue exclusion method, as described by Schinazi et al., Antimicrobial Agents and Chemotherapy, 22(3), 499 (1982). The $IC_{50}$ is the concentration of compound which inhibits 50% of normal cell growth.

Example 3

The anti-HIV activity of L-2'-A-5-FddC and L-3'-A-5-FddC was tested in CEM and PBM cells. The results are provided in Table 1.

TABLE 1

| Compound | Antiviral Activity $EC_{50}$ ($\mu M$) | Cytotoxicity $IC_{50}$ ($\mu M$) | Selectivity Index $IC_{50}/EC_{50}$ |
|---|---|---|---|
| L-2'-A-5-FddC (CEM) | 3.90 | >100 | >30 |
| L-3'-A-5-FddC (CEM) | 0.29 | >100 | >344 |
| L-2'-A-5-FddC (PBM) | 1.00 | >100 | >100 |
| L-3'-A-5-FddC (PBM) | 0.05 | >100 | >2647 |

Preparation of Pharmaceutical Compositions

Humans suffering from any of the disorders described herein, including AIDS, can be treated by administering to the patient an effective treatment amount of β-L-(2' or 3')-A-5-FddC as described herein, or a pharmaceutically acceptable prodrug or salt thereof in the presence of a phannaceutically acceptable carrier or diluent. The active materials can be administered by any appropriate route, for example, orally, parenterally, intravenously, intradermally, subcutaneously, or topically, in liquid or solid form.

The active compound is included in the pharmaceutically acceptable carrier or diluent in an amount sufficient to deliver to a patient a therapeutically effective amount of compound to inhibit viral replication in vivo, without causing serious toxic effects in the patient treated.

By "inhibitory amount" is meant an amount of active ingredient sufficient to exert an inhibitory effect as measured by, for example, an assay such as the ones described herein.

A preferred dose of the compound for all of the above mentioned conditions will be in the range from about 1 to 50 mg/kg, preferably 1 to 20 mg/kg, of body weight per day, more generally 0.1 to about 100 mg per kilogram body weight of the recipient per day. The effective dosage range of the pharmaceutically acceptable prodrug can be calculated based on the weight of the parent nucleoside to be delivered. If the prodrug exhibits activity in itself, the effective dosage can be estimated as above using the weight of the prodrug, or by other means known to those skilled in the art.

The compound is conveniently administered in unit any suitable dosage form, including but not limited to one containing 7 to 300 mg, preferably 70 to 1400 mg of active ingredient per unit dosage form. A oral dosage of 50–1000 mg is usually convenient, and more typically 50 to 500 mg.

Ideally the active ingredient should be administered to achieve peak plasma concentrations of the active compound of from about 0.2 to 70 $\mu$M, preferably about 1.0 to 10 $\mu$M. This may be achieved, for example, by the intravenous injection of a 0.1 to 5% solution of the active ingredient, optionally in saline, or administered as a bolus of the active ingredient.

The concentration of active compound in the drug composition will depend on absorption, inactivation, and excertion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intend to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such aws peppermint, methy salicylate, or orangr flavoring. When the dosage unit form is a capsule, it can contian, in addition to meterial of the above type, a liquid carrier such as a fatty oil. In addition, dosage unit forms can contain various other materials which modify the physical form of the dosage unit, for example, coatings of sugar, shellac, or other enteric agents.

The compound can be administered as a component of an elixir, suspension, syrup, water, chewing gum or the like. A syrup may contain, in addition to the active compounds, sucrose as a sweetening agent and certain preservatives, dyes and colorings and flavors.

The compound or a pharmaceutically acceptable derivative or salts thereof can also be mixed with other active material that do not impair the desired action, or with materials that supplement the desired action, such as antibiotics, antifimgals, antiinflammatories, protease inhibitors, or other nucleoside or nonnucleoside antiviral agents. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffer such as acetates, citrates or phosphates and agents for the adjustment of tonicity such as sodium chloride or dextrose. The parental preparation can be enclosed in ampoules, disposable syringes or multiple dose vbiats made of glass or plastic.

Tf administered intravenopusly, preferred carriers are physiological saline or phosphate buffered saline (PBS).

In a preferred embodiment, the active compounds are prepared with carriers that will protact the compound against rapid elimination from the bidy, such sa a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylacetic acid. Methods for preparation of such formulations well be apparent to those skilled in the art. The marerials can also be obtained commercially from Alza Corporation.

Liposomal suspensions (including liposomes targeted to infected cells with monoclonal antibodies to viral antigens) are also preferred as pharmaceutically acceptable carriers. These may be prepared according to methods known to those skilled in the art, for example, asdescribed in U.S. Pat. No. 4,522,811 (which is incorporated herein by reference in its entirety). For example, liposome formulations may be perpared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin a flim of dried lipid on the surface of the container. An aqueous slution of the active compound or its monophosphate, diphosphate, and/or triphosphate derivatives is then introduced into the container. The container is then swirled by hand to free lipid material from the sides of the container and to disperse lipid aggregates, thereby forming the liposomal suspension.

This invention has been described with reference to its preferred embodiments. Variations and modifications of the invention, will be obvious to those skilled in the art from the forgoing detailed description of the invention. It is intended that all of these varitions and modifications be included within the scope of this invention.

We claim:

1. A method for the treatment of HIV infection in a host comprising administering an effective amount of a $\beta$-L-(2'-azido)-2',3'-dideoxy-5-fluorocytidine compound or a pharmaceeutically acceptable ester, salt or prodrug thereof the fromula:

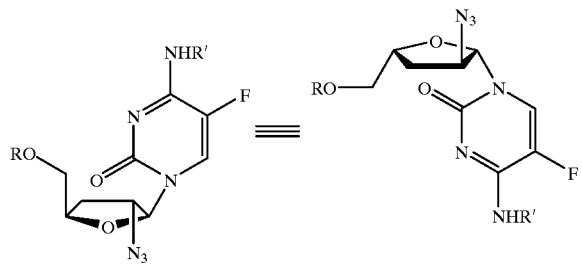

wherein R is H, acyl, monophosphate, diphosphate, or triphosphate, or a stabilized phosphate derivative (to form a stabilized nucleotide prodrug), and R' is H, acyl, or alkyl.

2. The method of claim 1, wherein R is H.
3. The method of claim 1, wherein R is acyl.
4. The method of claim 1, wherein R is monophosphate.
5. The method of claim 1, wherein R is diphosphate.
6. The method of claim 1, wherein R is triphosphate.

7. The method of claim 1, wherein R is a stbilized phosphate derivative.

8. A method for the treatment of HIV infection in a host comprising administering an effective amount of a β-L-(3'-azido)-2',3'-dideoxy-5-fluorocytidine compound or a pharmaceutically acceptable ester, salt or prodrng thereof of the formula:

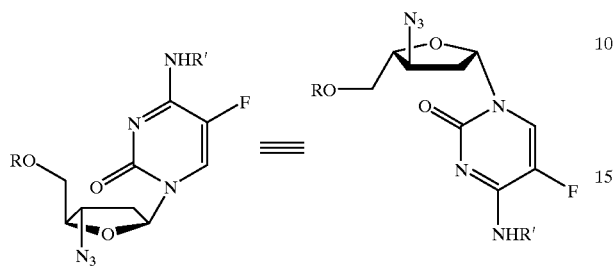

wherein R is H, acyl, monophosphate, diphosphate, or triphosphate, or a stabilized phosphate derivative (to form a stabilized nucleotide prodrug), R' is H, acyl, or alkyl.

9. The method of claim 8, wherein R is H.

10. The method of claim 8, wherein R is acyl.

11. The method of claim 8, wherein R is monophosphate.

12. The method of claim 8, wherein R is diphosphate.

13. The method of claim 8, wherein R is triphosphate.

14. The method of claim 8, wherein R is a stabilized phosphate derivative.

* * * * *